(12) United States Patent
Bakker et al.

(10) Patent No.: US 9,233,366 B2
(45) Date of Patent: Jan. 12, 2016

(54) CATALYSIS BY METAL NANOPARTICLES DISPERSED WITHIN A HIERARCHICALLY POROUS CARBON MATERIAL

(71) Applicant: Board of Trustees of The University of Alabama, Tuscaloosa, AL (US)

(72) Inventors: Martin G. Bakker, Tuscaloosa, AL (US); Franchessa Maddox Sayler, Tuscaloosa, AL (US); Kevin Shaughnessy, Tuscaloosa, AL (US)

(73) Assignee: Board of Trustees of The University of Alabama, Tuscaloosa, AL (US)

( * ) Notice: Subject to any disclaimer, the term of this patent is extended or adjusted under 35 U.S.C. 154(b) by 0 days.

(21) Appl. No.: 14/055,268

(22) Filed: Oct. 16, 2013

(65) Prior Publication Data

US 2014/0107371 A1    Apr. 17, 2014

Related U.S. Application Data

(60) Provisional application No. 61/714,281, filed on Oct. 16, 2012.

(51) Int. Cl.
*B01J 21/18* (2006.01)
*B01J 23/16* (2006.01)
(Continued)

(52) U.S. Cl.
CPC ............. *B01J 35/1076* (2013.01); *B01J 21/185* (2013.01); *B01J 23/42* (2013.01); *B01J 23/44* (2013.01); *B01J 23/462* (2013.01);
(Continued)

(58) Field of Classification Search
CPC ............ B01J 21/18; B01J 23/16; B01J 23/20; B01J 23/24; B01J 23/32; B01J 23/38; B01J 23/48; B01J 35/0053; B01J 35/006; B01J 35/10; B01J 35/1061; B01J 35/1076; B01J 37/0735; B01J 37/08; B01J 37/16
USPC ......................................... 502/182, 184, 185
IPC ........... B01J 21/18, 23/16, 23/20, 23/24, 23/32, B01J 23/38, 23/48, 35/0053, 35/006, 35/10, B01J 35/1061, 35/1076, 37/0735, 37/08, B01J 37/16
See application file for complete search history.

(56) References Cited

U.S. PATENT DOCUMENTS 3,404,030 A      10/1968   Palmateer
3,737,395 A  *   6/1973    Arnold et al. ................. 502/184
(Continued)

FOREIGN PATENT DOCUMENTS

KR       10-0751504 B1    8/2007
KR    10-2012-0105823 A    9/2012

OTHER PUBLICATIONS

International Search Report and Written Opinion issued in corresponding PCT Application No. PCT/US2013/065226 dated Dec. 18, 2013, 12 pgs.

(Continued)

*Primary Examiner* — Patricia L Hailey
(74) *Attorney, Agent, or Firm* — Meunier Carlin & Curfman LLC

(57) ABSTRACT

Disclosed are hierarchically porous carbon materials with a plurality of discreet nanoparticles dispersed on their carbon phase. The materials possess a continuous network of pores that spans the porous material, permitting the flow of fluids into and through the material. The porous materials can be used as heterogeneous catalysts.

20 Claims, 2 Drawing Sheets

(51) Int. Cl.

| | | |
|---|---|---|
| B01J 23/20 | (2006.01) | |
| B01J 23/24 | (2006.01) | |
| B01J 23/32 | (2006.01) | |
| B01J 23/38 | (2006.01) | |
| B01J 23/48 | (2006.01) | |
| B01J 35/10 | (2006.01) | |
| B01J 37/08 | (2006.01) | |
| B01J 37/16 | (2006.01) | |
| B01J 37/18 | (2006.01) | |
| B01J 23/42 | (2006.01) | |
| B01J 23/44 | (2006.01) | |
| B01J 23/46 | (2006.01) | |
| B01J 23/72 | (2006.01) | |
| B01J 23/755 | (2006.01) | |
| B01J 35/00 | (2006.01) | |
| B01J 37/02 | (2006.01) | |
| C07C 209/36 | (2006.01) | |
| C07C 2/86 | (2006.01) | |
| C07C 253/30 | (2006.01) | |
| C07C 67/343 | (2006.01) | |
| B82Y 30/00 | (2011.01) | |

(52) U.S. Cl.
CPC ............... *B01J 23/464* (2013.01); *B01J 23/72* (2013.01); *B01J 23/755* (2013.01); *B01J 35/002* (2013.01); *B01J 35/006* (2013.01); *B01J 35/0053* (2013.01); *B01J 35/1061* (2013.01); *B01J 35/1066* (2013.01); *B01J 37/0201* (2013.01); *B01J 37/08* (2013.01); *B01J 37/16* (2013.01); *B01J 37/18* (2013.01); *B82Y 30/00* (2013.01); *C07C 2/861* (2013.01); *C07C 67/343* (2013.01); *C07C 209/36* (2013.01); *C07C 253/30* (2013.01); *C07C 2521/18* (2013.01); *C07C 2523/44* (2013.01)

(56) References Cited

U.S. PATENT DOCUMENTS

| | | | | |
|---|---|---|---|---|
| 4,956,331 | A * | 9/1990 | Tsurumi et al. ............... | 502/339 |
| 6,398,962 | B1 | 6/2002 | Cabrera et al. | |
| 6,806,224 | B2 * | 10/2004 | Yoshihara et al. ............ | 502/185 |
| 6,911,192 | B2 | 6/2005 | Nakanishi | |
| 7,157,402 | B2 * | 1/2007 | Yu et al. ........................ | 502/185 |
| 7,374,599 | B1 | 5/2008 | Shelnutt et al. | |
| 7,449,165 | B2 | 11/2008 | Dai et al. | |
| 8,114,510 | B2 | 2/2012 | Dai et al. | |
| 2002/0128478 | A1 * | 9/2002 | Krska et al. ..................... | 544/59 |
| 2003/0181748 | A1 * | 9/2003 | Krauter et al. ................ | 556/441 |
| 2003/0187294 | A1 | 10/2003 | Hagemeyer et al. | |
| 2005/0079374 | A1 | 4/2005 | Asia | |
| 2005/0169829 | A1 * | 8/2005 | Dai et al. ................... | 423/445 R |
| 2005/0176990 | A1 * | 8/2005 | Coleman et al. ................ | 562/11 |
| 2006/0057051 | A1 | 3/2006 | Dai et al. | |
| 2006/0229466 | A1 * | 10/2006 | Arhancet et al. ............. | 562/531 |
| 2006/0258875 | A1 * | 11/2006 | Reyes et al. ................... | 558/357 |
| 2010/0010513 | A1 | 1/2010 | Yun et al. | |
| 2010/0140138 | A1 | 6/2010 | Chaumonnot et al. | |
| 2010/0210876 | A1 * | 8/2010 | Ryu et al. ...................... | 564/441 |
| 2011/0082024 | A1 * | 4/2011 | Liu et al. ............................ | 502/5 |
| 2011/0251053 | A1 | 10/2011 | Tucker et al. | |

OTHER PUBLICATIONS

Drisko et al., "One-Pot Synthesis of Hierarchically Structured Ceramic Monoliths with Adjustable Porosity", Chem. Mater. 2010, 22, 4379-4385.

Hao et. al. "Lysine-Assisted Rapid Synthesis of Crack-Free Hierarchical Carbon Monoliths with a Hexagonal Array of Mesopores", Carbon, 49:3762-3772 (2011).

Huang et al., "One-Step Hydrothermal Synthesis of Ordered Mesostructured Carbonaceous Monoliths with Hierarchical Porosities", Chem. Comm. 2008, 2641-2643.

Banhart et al., Metal Foams: Production and Stability, Adv. Eng. Mat. 8:781-794 (2006).

Bates et al., Block Copolymers—Designer Soft Materials, Physics Today 52(2):32-38 (1999).

Blanford et al., Gems of Chemistry and Physics: Macroporous Metal Oxides with 3D Order, Adv. Mat. 13:401-407 (2001).

Brockner et al., Thermal decomposition of nickel nitrate hexahydrate, Ni(NO3)2 •6H2O, in comparison to Co(NO3)2 •6H2O and Ca(NO3)2•4H2O, Thermochim. Acta 456:64-68 (2007).

Carn et al., Inorganic monoliths hierarchically textured via concentrated direct emulsion and micellar templates, J. Mater. Chem. 14:1370-1376 (2004).

Caruso et al., Silica Films with Bimodal Pore Structure Prepared by Using Membranes as Templates and Amphiphiles as Porogens, Adv. Functional Mat. 12(4):307-312 (2002).

Caruso et al., Cellulose Acetate Templates for Porous Inorganic Network Fabrication, Adv. Mat. 12(24):1921-1923 (2000).

Davis et al., Bacterial templating of ordered macrostructures in silica and silica-surfactant mesophases, Nature 385:420-423 (1997).

Estelle et al., Comparative study of the morphology and surface properties of nickel oxide prepared from different precursors, Solid State Ionics 156:233-243 (2003).

Fuller et al., Degradation of explosives-related compounds using nickel catalysts, Chemosphere 419-427 (2007).

Hu et al., Synthesis of Hierarchically Porous Carbon Monoliths with Highly Ordered Microstructure and Their Application in Rechargeable Lithium Batteries with High-Rate Capability, Adv. Functional Mater. 17(12):1873-1878 (2007).

Lepoutre et al., Detailed study of the pore-filling processes during nanocasting of mesoporous films using SnO2/SiO2 as a model system, Micro. Meso. Mater. 123:185-192 (2009).

Li et al., Controlling the Shape and Alignment of Mesopores by Confinement in Colloidal Crystals: Designer Pathways to Silica Monoliths with Hierarchical Porosity, Langmuir 23(7):3996-4004 (2007).

Llewellyn et al., Preparation of reactive nickel oxide by the controlled thermolysis of hexahydrated nickel nitrate, Solid State Ionics 101-103(2):1293-1298 (1997).

Lu et al., chapters 2 and 3, Nanocasting: A Versatile Strategy for Creating Nanostructured Porous Materials; Royal Society of Chemistry: Cambridge (2010).

Lu et al., Combined Surface and Volume Templating of Highly Porous Nanocast Carbon Monoliths, Adv. Functional Mater. 15:865-871 (2005).

Lu et al., Easy and flexible preparation of nanocasted carbon monoliths exhibiting a multimodal hierarchical porosity, Micro. Meso. Mater. 72:59-65 (2004).

Lu et al., Synthesis of Polyacrylonitrile-Based Ordered Mesoporous Carbon with Tunable Pore Structures, Chem. Mater. 16(1):100-103 (2004).

Maddox et al., Development of Ultrahigh Surface Area Porous Electrodes using Simultaneous and Sequential Meso- and Micro-structuring Methods, in Mobile Energy, Materials Research Society: Boston, vol. 1127E (2009).

Maekawa et al., Meso/Macroporous Inorganic Oxide Monoliths from Polymer Foams, Adv. Mat. 15(7-8):591-596 (2003).

Mansour, Spectroscopic and microscopic investigations of the thermal decomposition of nickel oxysalts. Part 2. Nickel nitrate hexahydrate, Thermochim. Acta 228(15):173-189 (1993).

Nakanishi, Pore Structure Control of Silica Gels Based on Phase Separation, J. Porous. Mat. 4(2):67-112 (1997).

Neimark et al., Theory of Preparation of Supported Catalysts, Ind. Eng. Chem. Prod. Res. Dev. 20:439-450 (1981).

Nishihara et al., Ordered Macroporous Silica by Ice Templating, Chem. Mater. 17(3):683-689 (2005).

Paulik et al., Investigation of the Phase Diagram for the System Ni(NO3)2-H2O and Examination of the Decomposition of Ni(NO3)2 6H2O, Thermochim. Acta 121:137-149 (1987).

Ryoo et al., Ordered Mesoporous Carbons, Adv. Mat. 13(9):677-681 (2001).

(56) References Cited

OTHER PUBLICATIONS

Sholklapper et al., Synthesis of Dispersed and Contiguous Nanoparticles in Solid Oxide Fuel Cell Electrodes, Fuel Cells 5:303-312 (2008).

Sietsma et al., Ordered Mesoporous Silica to Study the Preparation of Ni/SiO2 ex Nitrate Catalysts: Impregnation, Drying, and Thermal Treatments, Chem. Mater. 20(9):2921-2931 (2008).

Sietsma et al., How nitric oxide affects the decomposition of supported nickel nitrate to arrive at highly dispersed catalysts, J. Catal. 260:227-235 (2008).

Smått et al., Synthesis of micrometer sized mesoporous metal oxide spheres by nanocasting, Micro. Meso. Mater. 112:308-318 (2008).

Smått et al., Hierarchically Porous Metal Oxide Monoliths Prepared by the Nanocasting Route, Chem. Mater. 18:1443-1450 (2006).

Smått et al., Hierachically porous nanocrystalline cobalt oxide monoliths through nanocasting, Chem. Comm. 19:2188-2189 (2004).

Smått et al., Versatile Double-Templating Synthesis Route to Silica Monoliths Possessing a Multimodal Hierarchical Porosity, Chem. Mater. 15:2354-2361 (2003).

Stein et al., Morphological Control in Colloidal Crystal Templating of Inverse Opals, Hierarchical Structures, and Shaped Particles, Chem. Mater. 20(3):649-666 (2008).

Stein, Sphere templating methods for periodic porous solids, Micro. Meso. Mater. 44-45:227-239 (2001).

Sturm et al., Tin Dioxide Microspheres as a Promising Material for Phosphopeptide Enrichment Prior to Liquid Chromatography—(Tandem) Mass Spectrometry Analysis, Adv. Functional Mater. 18(16):2381-2389 (2008).

Sun et al., Container Effect in Nanocasting Synthesis of Mesoporous Metal Oxides, J. Am. Chem. Soc. 133 (37):14542-14545 (2011).

Suzuki et al., Synthesis of mesoporous silica foams with hierarchical trimodal pore structures, J. Mater. Chem. 13:1812-1816 (2003).

Tappan et al., Nanoporous Metal Foams, Angew. Chem. Int. Ed. 49:4544-4565 (2010).

Tappan et al., Ultralow-Density Nanostructured Metal Foams: Combustion Synthesis, Morphology, and Composition, J. Am. Chem. Soc. 128(20):6589-6594 (2006).

Vargas-Florencia et al., Inorganic Salt Hydrates as Cryoporometric Probe Materials to Obtain Pore Size Distribution, J. Phys Chem. B 110:3867-3870 (2006).

Walsh et al., Dextran templating for the synthesis of metallic and metal oxide sponges, Nat. Mat. 2:386-390 (2003).

Yan et al., A Chemical Synthesis of Periodic Macroporous NiO and Metallic Ni, Adv. Mat. 11(12):1003-1006 (1999).

Yang et al., Synthesis of replica mesostructures by the nanocasting strategy, J. Mater. Chem. 15:1217-1231 (2005).

Yue et al., Synthesis of Porous Single Crystals of Metal Oxides via a Solid-Liquid Route, Chem. Mater. 19(9):2359-2363 (2007).

Yue et al., Mesoporous metal oxides templated by FDU-12 using a new convenient method, Studies Surf. Sci. Catal. 170:1755-1762 (2007).

Zhao et al., Multiphase Assembly of Mesoporous-Macroporous Membranes, Chem. Mater. 11(5):1174-1178 (1999).

Beletskaya et al., The Heck Reaction as a Sharpening Stone of Palladium Catalysis, Chem. Rev. 100:3009-3066 (2000).

Belfield et al., Synthesis of New Two-Photon Absorbing Fluorene Derivatives via Cu-Mediated Ullmann Condensations, The Journal of Organic Chemistry 65(15):4475-4481 (2000).

USPTO, Office Action for U.S. Appl. No. 14/046,062, mailed Jun. 5, 2015.

Lee, J-H, "Gas sensors using hierarchical and hollow oxide nanostructures: Overview," Sensors and Actuators vol. B 140, 2009, pp. 319-336.

Zhu, J., et al., "Hierarchical porous/hollow tin oxide nanostructures mediated by polypeptide: surface modification, characterization, formation mechanism and gas-sensing properties," Nanotechnology, vol. 17, 2006, pp. 5960-5969.

Final Office Action, dated Nov. 6, 2015, received in connection with U.S. Appl. No. 14/046,062.

* cited by examiner

CATALYSIS BY METAL NANOPARTICLES DISPERSED WITHIN A HIERARCHICALLY POROUS CARBON MATERIAL

CROSS REFERENCE TO RELATED APPLICATIONS

This application claims the benefit of U.S. Provisional Application No. 61/714,281, filed Oct. 16, 2012, which is hereby incorporated herein by reference in its entirety.

STATEMENT REGARDING FEDERALLY SPONSORED RESEARCH OR DEVELOPMENT

This invention was made with Government Support under Grant No. IPP-1237216 awarded by the National Science Foundation. The Government has certain rights to the invention.

FIELD

The present disclosure is generally related to catalytic metal nanoparticles supported on a hierarchically porous carbon material, as well as methods of making and using thereof.

BACKGROUND

Heterogeneous catalysts, including inorganic nanoparticles supported on carbon, are widely used to increase the rates of many chemical reactions. For small scale applications typical of research or development environments, catalysts are often provided in the form of a fine powder to provide maximum surface area. Catalyst powders are then added to a liquid containing the reactants. Once the reaction is complete, the catalyst must be separated from the solution, typically by filtration. When performing reactions at larger scales, such as in industrial settings, catalysts are often provided in the form of a fixed bed of particles or pellets. In these cases, reactions are typically performed as the reactants flow over or though the fixed bed. For example, the fixed bed is then contacted with the fluid reactants, with the reaction proceeding while the fluid is in contact with the catalyst. After an appropriate time in contact with the fixed catalyst bed, the fluid, which now contains the product of the chemical reaction, continues on for further processing.

Despite the wide use of heterogeneous catalysts in both industrial and research settings, existing catalysts suffer from a number of shortcomings; among these are inefficient use of precious metals, limited life time, and a tendency to be pyrophoric in contact with air. For research and development environments, the need to carry out a filtration step can be disadvantageous, particularly in the case of finely divided and/or pyrophoric catalysts. For larger scale applications in which a fluid containing the reactants flows over a fixed catalyst bed, the transport of the fluid through the catalyst bed can limit the rate of the reaction, and require larger pumps because of the pressure drop through the catalyst bed. Further, unwanted reactions can produce high molecular weight products which clog the pore spaces within and between the catalysts decreasing the activity of the catalyst, and the effective lifetime of the catalyst.

SUMMARY

Hierarchically porous carbon materials comprising a plurality of discreet nanoparticles are provided. The hierarchically porous materials comprise a plurality of macropores that interconnect, forming a continuous network of pores spanning the porous material. The continuous network of pores permits the flow of liquid or gas into and through the hierarchically porous material. In some embodiments, the macropores have a diameter of from about 0.1 µm to about 50 µm. The walls of the macropores comprise a plurality of mesopores, thereby forming a hierarchically porous material. In some embodiments, the mesopores have a diameter of from about 2 nm to about 50 nm. The walls of the macropores and mesopores comprise a continuous carbon phase on which is dispersed a plurality of discreet nanoparticles.

In some cases, the nanoparticles are inorganic nanoparticles formed from a catalytically active metal, metal oxide, or combinations thereof. For example, the nanoparticles can be formed from a metal selected from the group consisting of Ti, V, Cr, Mn, Fe, Co, Ni, Cu, Zr, Nb, Mo, Tc, Ru, Rh, Pd, Ag, Hf, Ta, W, Re, Os, Ir, Pt, Au, La, Ce, Pr, Nd, Pm, Sm, Eu, Gd, Tb, Dy, Ho, Er, Tm, Yb, and combinations thereof.

Characteristics of the nanoparticles, including particle size and specific surface area, can be varied in view of the desired application for the hierarchically porous material. For example, the nanoparticles can have an average particle size of from about 2 nm to about 50 nm. In some cases, the nanoparticles can have a specific surface area of from about 500 $m^2/g$ of nanoparticles to about 2000 $m^2/g$ of nanoparticles. The nanoparticles can also be incorporated into the hierarchically porous material in varying amounts. For example, the nanoparticles can be present in an amount from greater than 0% by weight to about 30% by weight, based on the total weight of the hierarchically porous material.

Also provided are methods for preparing the hierarchically porous materials described herein. The hierarchically porous materials can be prepared by contacting a hierarchically porous carbon material with a composition comprising a metal salt (typically at reduced pressure), and reacting the metal salt to produce metal and/or metal oxide nanoparticles dispersed throughout the hierarchically porous material. For example, the metal salt can be reduced to form nanoparticles by contacting the metal salt with a reducing agent, such as hydrogen gas. The metal salt can also be reduced by heating the metal salt to above the decomposition temperature of the metal salt.

The hierarchically porous materials described herein can be used as heterogeneous catalysts. For example, the materials can be employed as catalysts in cross-coupling reactions, such as Heck couplings, Suzuki couplings, Sonogashira couplings, Hiyama couplings, Negishi couplings, Kumada couplings, Stille couplings, Buchwald-Hartwig couplings, and Fukuyama couplings. The materials can also be used to catalyze other types of reactions, including catalytic hydrogenation reactions and catalytic hydrogenolysis reactions.

DETAILED DESCRIPTION

General Definitions

Figure 1:
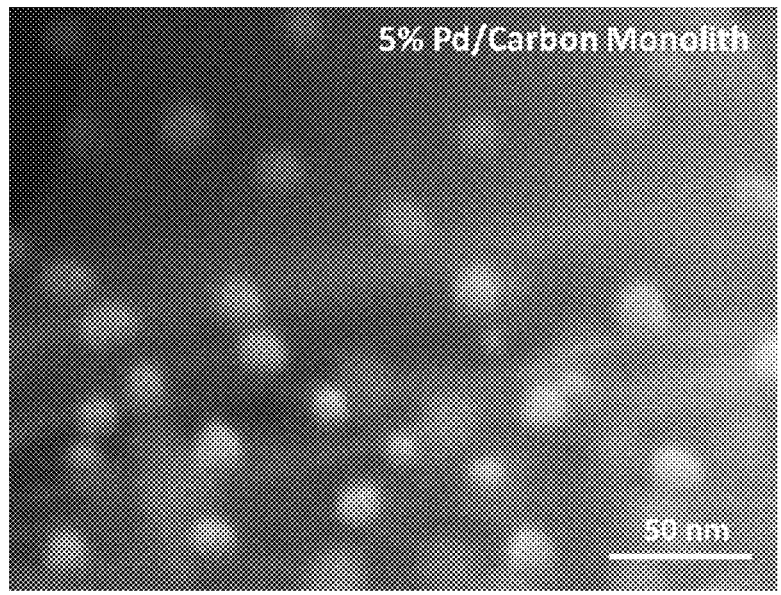
FIG. 1 is a scanning electron microscopy (SEM) image of Pd nanoparticles dispersed in a hierarchically porous carbon monolith (scale bar=50 nm). The carbon monolith was loaded with 5% by weight Pd nanoparticles. The SEM image confirmed the presence of well dispersed Pd nanoparticles having an average diameter of 7 nm within the hierarchically porous carbon monolith.

"Phase," as used herein, generally refers to a region of material having a substantially uniform composition which is a distinct and physically separate portion of a heterogeneous system. The term "phase" does not imply that the material making up a phase is a chemically pure substance, but merely that physical properties of the material making up the phase are essentially uniform throughout the material, and that these physical properties differ significantly from the physical properties of another phase within the material. Examples of physical properties include density, index of refraction, and chemical composition.

"Continuous," as used herein, generally refers to a phase such that all points within the phase are directly connected, so that for any two points within a continuous phase, there exists a path which connects the two points without leaving the phase. A "phase" in this context can refer to, for example, a pore or network of pores, a void, or a wall formed from a solid layer of carbon.

"Bicontinuous," as used herein, generally refers to a material containing two separate continuous phases such that each phase is continuous, and in which the two phases are interpenetrating, such that it is impossible to separate the two structures without tearing one of the structures. Another example of a system with this property is the gyroid phase of block copolymers. See, for example, Bates, "Block Copolymers—Designer Soft Materials", *Physics Today* Feb. 32, 1999, which is incororated by reference herein for its description of bicontinuous materials.

"Tortuous," as used herein, generally refers to a phase that is characterized by numerous short straight line distances, such that moving within the phase requires continual changes in direction.

By "hollow" is meant when two continuous (void) network phases completely separated by a third continuous phase that prevents any direct contact between the two continuous void network phases. In a large body, material cannot travel from one continuous void phase to the other continuous void phase without passing through the third continuous separating phase.

"Hierarchical pores," as used herein, generally refer to pores that span two or more different length scales. Thus, "hierarchically porous materials" are materials which contain pores that span two or more length scales. In some embodiments, there can be a distribution of pore diameters at each length scale, where often the distributions of pore diameters are sufficiently narrow that there is little or no overlap between the pore size distributions. In some cases, there are some pore sizes for which few or no pores are present in such a hierarchically porous material.

"Constant diameter," as used herein, generally refers to a circumstance in which the smallest distance across a continuous phase is relatively constant (e.g., less than one standard deviation, or less than two standard deviations).

"Monolith," as used herein, generally refers to a macroscopic, single piece of material typically with one or more dimensions (length, width, and/or height) exceeding about 0.1 mm. A monolith is distinguished from a particle, in that particles possess dimensions that are less than that for a monolith.

"Particle," as used herein, generally refers to a discrete unit of material, such as a grain, bead, or other particulate form, typically with dimensions (length, width, and/or height) ranging from 1 µm to 100 µm. Particles may have any shape (e.g., spherical, ovoid, or cubic).

"Nanoparticle", as used herein, generally refers to a particle of any shape having an average particle size from about 1 nm up to, but not including, about 1 micron. In certain embodiments, nanoparticles have an average particle size from about 2 nm to about 50 nm. The size of nanoparticles can be experimentally determined using a variety of methods known in the art, including electron microscopy.

"Mean particle size" or "average particle size", are used interchangeably herein, and generally refer to the statistical mean particle size (diameter) of the nanoparticles in a population of nanoparticles. The diameter of an essentially spherical nanoparticle may refer to the physical or hydrodynamic diameter. The diameter of a non-spherical nanoparticle may refer preferentially to the hydrodynamic diameter. As used herein, the diameter of a non-spherical nanoparticle may refer to the largest linear distance between two points on the surface of the nanoparticle. Mean particle size can be measured using methods known in the art, such as evaluation by scanning electron microscopy.

"Monodisperse" and "homogeneous size distribution" are used interchangeably herein, and generally describe a population of nanoparticles where all of the nanoparticles are the same or nearly the same size. As used herein, a monodisperse distribution refers to particle distributions in which 90% of the distribution lies within 25% of the median particle size (e.g., within 20% of the median particle size, within 15% of the median particle size, within 10% of the median particle size, or within 5% of the median particle size).

Hierarchically Porous Materials

Hierarchically porous materials comprising a plurality of discreet nanoparticles are herein described. The hierarchically porous materials comprise a plurality of macropores that interconnect, forming a continuous network of pores that spans the porous material. The walls of the macropores comprise a plurality of mesopores, thereby forming a hierarchically porous material. The walls of the macropores and mesopores comprise a continuous carbon phase on which is dispersed a plurality of discreet nanoparticles.

The materials can be described as porous. As such, the materials possess a plurality of pores, holes, and/or channels, each of which may or may not extend throughout the entire length of the material. The pores can interconnect, resulting in a network of pores or voids that spans the material, permitting the flow of liquid or gas into and through the material, i.e., a continuous phase of pores or voids. The materials can also be described as bicontinuous (i.e., the materials have two or more continuous phases), meaning that both a voids/pore phase and a carbon phase are continuous throughout the material.

The materials are hierarchically porous. As described above, hierarchical porous materials have pores that span two or more length scales. The materials described herein possess both macropores and mesopores. In some embodiments, the materials can optionally further contain micropores.

The materials comprise a plurality of macropores. Macropores are pores or voids having a diameter greater than about 0.1 µm. For example, the macropores can have a diameter greater than about 0.5 µm, greater than about 0.75 µm, greater than about 1.0 µm, greater than about 1.5 µm, greater than about 2.0 µm, greater than about 2.5 µm, greater than about 5 µm, greater than about 10 µm, greater than about 15 µm, or greater. In some embodiments, the macropores have a diameter of less than about 50 µm (e.g., less than about 40 µm, less than about 30 µm, less than about 25 µm, less than about 20 µm, less than about 15 µm, less than about 10 µm, less than about 7.5 µm, less than about 5 µm, less than about 2.5 µm, less than about 2.0 µm, less than about 1.5 µm, less than about 1.0 µm, less than about 0.75 µm, less than about 0.5 µm, less than about 0.25 µm, or less).

The macropores can have a diameter ranging from any of the minimum values to any of the maximum values described above. In some embodiments, the macropores have a diameter of from about 0.1 µm to about 50 µm. In certain instances, the macropores have a diameter of from about 0.5 µm to about 30 µm, from about 1 µm to about 20 µm, from about 5 µm to about 15 µm, from about 10 µm to about 30 µm, or from about 0.5 µm to about 15 µm in diameter. The macropores can have a substantially constant diameter along their length.

In some embodiments, the diameter of the macropores is substantially constant from macropore to macropore throughout the material, such that substantially all (e.g., at least 75%, at least 80%, at least 85%, at least 90%, or at least 95%) of the macropores in the material have a diameter that is within 40% of the average macropore's diameter (e.g., within 35% of the average macropore's diameter, within 30% of the average macropore's diameter, within 25% of the average macropore's diameter, within 20% of the average macropore's diameter, within 15% of the average macropore's diameter, or within 10% of the average macropore's diameter).

The walls of the macropores are formed from a continuous carbon phase. In some embodiments, the walls have a thickness of from about 50 nm to about 15 µm, for example, from about 50 nm to about 600 nm, 100 nm to about 500 nm, from about 200 to about 400 nm, from about 50 to about 200, from about 300 to about 600 nm, from about 500 nm to about 5 µm, from about 5 µm to about 10 µm, or from about 5 µm to about 15 µm.

The walls of the macropores comprise a plurality of mesopores, thereby forming a hierarchically porous material. Mesopores are pores, holes, voids, and/or channels having a diameter ranging from about 2 nm to about 50 nm.

For example, the mesopores can have a diameter greater than about 2 nm, greater than about 3 nm, greater than about 4 nm, greater than about 5 nm, greater than about 7.5 nm, greater than about 10 nm, greater than about 15 nm, greater than about 20 nm, greater than about 25 nm, greater than about 30 nm, or greater. In some embodiments, the mesopores have a diameter of less than about 50 nm (e.g., less than about 40 nm, less than about 35 nm, less than about 30 nm, less than about 25 nm, less than about 20 nm, less than about 15 nm, less than about 10 nm, less than about 7.5 nm, less than about 6 nm, less than about 5 nm, or less). For example, the mesopores can have a diameter ranging from about 2 nm to about 30 nm, from about 10 nm to about 20 nm, from about 15 nm to about 50 nm, from about 2 nm to about 6 nm, or from about 2 nm to about 15 nm in diameter.

The mesopores can have a substantially constant diameter along their length. In some embodiments, the diameter of the mesopores is substantially constant from mesopore to mesopore throughout the material, such that substantially all (e.g., at least 75%, at least 80%, at least 85%, at least 90%, or at least 95%) of the mesopores in the material have a diameter that is within 40% of the average mesopore's diameter (e.g., within 35% of the average mesopore's diameter, within 30% of the average mesopore's diameter, within 25% of the average mesopore's diameter, within 20% of the average mesopore's diameter, within 15% of the average mesopore's diameter, or within 10% of the average mesopore's diameter).

The walls of the mesopores are formed from a continuous carbon phase. In some embodiments, the walls have a thickness of from about 5 nm to about 15 µm, for example, from about 5 nm to about 10 µm, from about 5 nm to about 5 µm, from about 5 nm to about 1 µm, from about 5 nm to about 800 nm, from about 5 nm to about 600 nm, from about 5 nm to about 500 nm, from about 5 nm to about 400 nm, from about 5 nm to about 200 nm, from about 5 nm to about 10 nm, from about 5 nm to about 50 nm, or from about 5 nm to about 25 nm. In some instances the walls have a thickness of greater than 5 nm (e.g., greater than 10 nm, greater than 15 nm, greater than 20 nm, or greater).

In some embodiments, the walls of the macropores, mesopores, or combinations thereof further contain micropores. Micropores are pores, holes, and/or channels that have a diameter of less than about 2 nm. For example, micropores can have a diameter ranging from about 0.5 nm to 2 nm. The walls of the micropores can be formed from a continuous carbon phase.

The hierarchically porous materials described herein can be characterized as possessing two or more continuous phases (e.g., a void phase and a carbon phase). The two or more phases are generally tortuous, such that the two or more phases are interpenetrating.

In some embodiments, substantially all of the pores in the hierarchically porous material are open pores, and substantially none of the pores are closed pores. Closed pores are defined as pores which are completely surrounded by solid material, whereas open pores are defined as pores that are not completely surrounded by solid material. Thus in open porous materials (i.e., porous materials wherein substantially all of the pores in the porous material are open pores), substantially all of the pores in the material are part of a continuous void phase.

In certain embodiments, the hierarchically porous materials can comprise two continuous void phases that are completely separated by a third continuous carbon phase that prevents any direct contact between the two continuous void phases. Such materials may be said to be hollow. In these embodiments, the carbon phase can be optionally porous on a much smaller scale than the void phases. When the hierarchically porous materials have a hollow geometry, they can optionally be even-walled. In even-walled materials, the third continuous carbon phase that separates the two continuous void phases is of substantially constant thickness, such that the distance between one continuous void phase and the other continuous void phase is substantially constant throughout the material.

The hierarchically porous materials described herein are structurally distinct from foams. Foams can exist in two primary forms. In closed-cell foams, void regions are completely enclosed within a continuous solid region. Such closed-cell foams are not bicontinuous. Open-cell foams can be bicontinuous; however, open-cell foams possess a the void network that is disordered. Specifically, the diameters of the pores in open-cell foams vary greatly over a large range, often with large spherical voids separated from each other by small windows. In contrast, the hierarchically porous materials described herein are bicontinuous, and can have a narrow pore size distribution (e.g., less than two standard deviations in pore diameter, or less than one standard deviation in diameter).

The hierarchically porous materials are not etch materials, whereby ionizing radiation is used to form the pores. In some embodiments, the hierarchically porous materials are substantially free (i.e., having less than about 1% by weight of the porous material) of surfactant. In some embodiments, the hierarchically materials are substantially free (having less than about 1, 0.1, or 0.01% by weight of the porous material) of silica. In some embodiments, the continuous carbon phase is substantially free (having less than about 1, 0.1, or 0.01% by weight of the porous material) of metals or metal oxides.

The hierarchically porous materials described herein can have very high surface areas. For example, the surface area can be greater than about 50, 75, 100, 200, 400, 600, 800, 1000, 1200, 1400, 1600, 1800, or 2000 $m^2/g$ material, where any of the values described above can be the upper or lower endpoint of a surface area range. In some examples, the hierarchically porous material has a surface area that ranges from about 200 $m^2/g$ material to about 2000 $m^2/g$ material.

In some embodiments, the hierarchically porous material is a monolith. For example, the hierarchically porous material can be a macroscopic, single piece of material typically with one or more dimensions (length, width, and/or height) exceeding about 0.1 mm (e.g., at least about 0.2 mm, at least about 0.4 mm, at least about 0.5 mm, at least about 0.6 mm, at least about 0.8 mm, at least about 1.0 mm, at least about 1.5 mm, or greater). In some instances, the hierarchically porous material possesses more than one dimension that is greater than about 0.1 mm. In other embodiments, the hierarchically porous material can be a particle. Particulate materials can be formed from monolithic materials using particle size reduction techniques such grinding, milling (e.g., air-attrition milling (jet milling) or ball milling).

The hierarchically porous materials further comprise a plurality of discreet nanoparticles. The nanoparticles are dispersed on the carbon phase of the hierarchically porous material. As such, the hierarchically porous material serves as a solid support for the nanoparticles.

The nanoparticles can be evenly dispersed throughout the hierarchically porous material, such that the concentration of nanoparticles deposited on the carbon phase near the surface of the hierarchically porous material is substantially similar to the concentration of nanoparticles deposited on the carbon phase near the interior of the hierarchically porous material. In certain embodiments, the concentration of nanoparticles present in the interior of the hierarchically porous material, when measured as the weight percent of metal atoms present in the interior of the hierarchically porous material as determined using energy dispersive x-ray spectroscopy, is within 50% (e.g., within 45%, within 40%, within 35%, within 30%, within 25%, within 20%, within 15%, within 10%, or within 5%) of the concentration of nanoparticles present on the exterior of the hierarchically porous material, when measured as the weight percent of metal atoms present on the exterior of the hierarchically porous material as determined using energy dispersive x-ray spectroscopy.

In addition, the nanoparticles can be evenly dispersed on the carbon phase, such that the distance between adjacent particles deposited on the carbon phase is relatively consistent. In these cases, the nanoparticles are not present as aggregates or agglomerates on the carbon phase. The resulting hierarchically porous materials possess a plurality of discreet nanoparticles evenly dispersed walls of the macropores and mesopores. In some embodiments, the nanoparticles are dispersed on the carbon phase such that the average distance between adjacent nanopartices on the carbon phase, as determined by analysis of scanning electron microscopy micrographs, is at least 0.5 times the average nanoparticle diameter (e.g., at least 0.75 times the average nanoparticle diameter, at least the average nanoparticle diameter, at least 1.5 times the average nanoparticle diameter, at least 2 times the average nanoparticle diameter, at least 2.5 times the average nanoparticle diameter, at least 3 times the average nanoparticle diameter, at least 5 times the average nanoparticle diameter, at least 7.5 times the average nanoparticle diameter, at least 10 times the average nanoparticle diameter, at least 15 times the average nanoparticle diameter, at least 20 times the average nanoparticle diameter, at least 25 times the average nanoparticle diameter, at least 50 times the average nanoparticle diameter, or at least 100 times the average nanoparticle diameter.

In some cases, the nanoparticles are inorganic nanoparticles formed from a catalytically active metal, metal oxide, or combinations thereof. For example, the nanoparticles can be formed from a metal selected from the group consisting of Ti, V, Cr, Mn, Fe, Co, Ni, Cu, Zr, Nb, Mo, Tc, Ru, Rh, Pd, Ag, Hf, Ta, W, Re, Os, Ir, Pt, Au, La, Ce, Pr, Nd, Pm, Sm, Eu, Gd, Tb, Dy, Ho, Er, Tm, Yb, and combinations thereof.

Characteristics of the nanoparticles, including particle size and specific surface area, can be varied in view of the desired application for the hierarchically porous material. Generally, the nanoparticles have an average particle size that is smaller than the diameter of the mesopores. In some embodiments, the nanoparticles have an average particle size, as determined by scanning electron microscopy, of at least about 2 nm (e.g., at least about 5 nm, at least about 10 nm, at least about 15 nm, at least about 25 nm, at least about 35 nm, or greater). In some embodiments, the nanoparticles have an average particle size of less than about 50 nm (e.g., less than about 45 nm, less than about 40 nm, less than about 35 nm, less than about 30 nm, less than about 25 nm, less than about 20 nm, less than about 15 nm, less than about 10 nm, less than about 5 nm, or less).

The nanoparticles can have an average particle size ranging from any of the minimum values to any of the maximum values described above. In certain embodiments, the nanoparticles have an average particle size ranging from about 2 nm to about 50 nm (e.g., ranging from about 2 nm to about 30 nm, ranging from about 5 nm to about 10 nm, or ranging from about 5 nm to about 20 nm).

In some embodiments, the population of nanoparticles is a monodisperse population of particles. In other embodiments, the population of nanoparticles is a polydisperse population of nanoparticles. In some instances where the population of nanoparticles is polydisperse, greater that 50% of the particle size distribution (e.g., greater than 60% of the particle size distribution, greater than 70% of the particle size distribution, greater than 75% of the particle size distribution, greater than 80% of the particle size distribution, greater than 85% of the particle size distribution, or greater than 90% of the particle size distribution) lies within 10% of the median particle size.

In some embodiments, the nanoparticles can have a specific surface area of at least about 1 $m^2/g$ of nanoparticles (e.g., at least about 1 $m^2/g$ of nanoparticles, at least about 5 $m^2/g$ of nanoparticles, at least about 10 $m^2/g$ of nanoparticles, at least about 15 $m^2/g$ of nanoparticles, at least about 25 $m^2/g$ of nanoparticles, at least about 50 $m^2/g$ of nanoparticles, at least about 100 $m^2/g$ of nanoparticles, at least about 200 $m^2/g$ of nanoparticles, at least about 250 $m^2/g$ of nanoparticles, at least about 300 $m^2/g$ of nanoparticles, at least about 400 $m^2/g$ of nanoparticles, at least about 500 $m^2/g$ of nanoparticles, at least about 600 $m^2/g$ of nanoparticles, at least about 750 $m^2/g$ of nanoparticles, at least about 800 $m^2/g$ of nanoparticles, at least about 900 $m^2/g$ of nanoparticles, at least about 1000 m²/g of nanoparticles, at least about 1250 m²/g of nanoparticles, at least about 1500 m²/g of nanoparticles, at least about 1750 m²/g of nanoparticles, or greater). In some embodiments, the nanoparticles have specific surface area of less than about 2000 m²/g of nanoparticles (e.g., less than about 1750 m²/g of nanoparticles, less than about 1500 m²/g of nanoparticles, less than about 1250 m²/g of nanoparticles, less than about 1000 m²/g of nanoparticles, less than about 750 m²/g of nanoparticles, less than about 500 m²/g of nanoparticles, less than about 400 m²/g of nanoparticles, less than about 300 m²/g of nanoparticles, less than about 250 m²/g of nanoparticles, less than about 200 m²/g of nanoparticles, less than about 100 m²/g of nanoparticles, less than about 50 m²/g of nanoparticles, less than about 25 m²/g of nanoparticles, less than about 15 m²/g of nanoparticles, less than about 10 m²/g of nanoparticles, less than about 5 m²/g of nanoparticles, or less).

The nanoparticles can have specific surface area ranging from any of the minimum values to any of the maximum values described above. In some embodiments, the nanoparticles have a surface area of from about 1 m²/g of nanoparticles to about 2000 m²/g of nanoparticles. In certain embodiments, the nanoparticles can have a large specific surface area (e.g., from about 500 m²/g of nanoparticles to about 2000 m²/g of nanoparticles).

The nanoparticles can also be incorporated into the hierarchically porous material in varying amounts. In some instances, the nanoparticles are present in an amount greater than 0% by weight (e.g., greater than about 0.1% by weight, greater than about 0.25% by weight, greater than about 0.5% by weight, greater than about 0.75% by weight, greater than about 1% by weight, greater than about 1.5% by weight, greater than about 2% by weight, greater than about 2.5% by weight, greater than about 5% by weight, greater than about 10% by weight, greater than about 15% by weight, greater than about 20% by weight, or greater), based on the total weight of the hierarchically porous material. The nanoparticles can be present in an amount less than about 30% by weight (e.g., less than about 25% by weight, less than about 20% by weight, less than about 15% by weight, less than about 10% by weight, less than about 5% by weight, less than about 2.5% by weight, less than about 2% by weight, less than about 1.5% by weight, less than about 1% by weight, or less than about 0.5% by weight), based on the total weight of the hierarchically porous material.

The nanoparticles can be present in a range from any of the minimum values to any of the maximum values described above. For example, the nanoparticles can be present in an amount from greater than 0% by weight to about 30% by weight, based on the total weight of the hierarchically porous material (e.g., from about 25% by weight to about 30% by weight, from about 0.1% by weight to about 10% by weight, or from about 0.1% by weight to about 1.5% by weight).

In certain embodiments, the hierarchically porous materials do not release nanoparticles when contacted with a fluid.

Methods of Making

Also provided are methods of making the hierarchically porous materials described above. The hierarchically porous materials can be prepared by contacting a hierarchically porous carbon material with a composition comprising a metal salt (typically at reduced pressure), and reducing the metal salt to produce metal and/or metal oxide nanoparticles dispersed throughout the hierarchically porous material.

Suitable hierarchically porous carbon materials can be formed by depositing a carbon phase within a non-carbon (e.g., silica) template. Porous templates can be obtained commercially, or can be prepared according to methods described in the art. For example, a number of groups have used colloidal crystal templating or self-assembly of polymer or silica beads to give a relatively hard template into which the metal salts disclosed herein can be infiltrated to create the disclosed metal and/or metal oxide porous material. Infiltration of a sol-gel precursor including a surfactant as template can be used to induce ordered mesopores in the macropore walls of these materials (Li et al., "Controlling the Shape and Alignment of Mesopores by Confinement in Colloidal Crystals: Designer Pathways to Silica Monoliths with Hierarchical Porosity", *Langmuir* 23:3996, 2007). The major drawback of this approach is the expense of the polymeric beads for macroscopic pieces.

Porous templates can also be prepared using microemulsions (Cam et al., "Inorganic monoliths hierarchically textured via concentrated direct emulsion and micellar templates", *J. Mater. Chem.* 14:1370, 2004), bicontinuous polymer foams (Maekawa et al., "Meso/Macroporous Inorganic Oxide Monoliths from Polymer Foams", *Adv. Mat.* 15:591, 2003), salt crystals (Zhao et al., "Multiphase Assembly of Mesoporous-Macroporous Membranes", *Chem. Mater.* 11:1174, 1999), bacteria (Davis et al., "Bacterial templating of ordered macrostructures in silica and silica-surfactant mesophases", *Nature*, 385:420, 1997), cellulose (Caruso et al., "Silica Films with Bimodal Pore Structure Prepared by Using Membranes as Templates and Amphiphiles as Porogens", *Adv. Functional Mater.* 12:307, 2002; Caruso et al., "Cellulose Acetate Templates for Porous Inorganic Network Fabrication", *Adv. Mat.*, 12:1921, 2000), sugars (Walsh et al., "Dextran templating for the synthesis of metallic and metal oxide sponges", *Nat. Mat.* 2:386, 2003), or ice (Nishihara et al., "Ordered Macroporous Silica by Ice Templating", *Chem. Mater.* 17:683, 2005) as templates for macrostructure, and foaming of the sol-gel silica (Suzuki et al., "Synthesis of mesoporous silica foams with hierarchical trimodal pore structures", *J. Mater. Chem.* 13:1812, 2003). Each of these articles is incorporated herein by reference for their teaching of processes for producing porous templates.

Suitable porous templates can comprise silica, metal, or metal oxide. In other examples, the porous template comprises a combination or composite of one or more of silica, carbon, metal, or metal oxide. In some embodiments, the porous template is a hierarchically porous silica monoliths, as prepared by the methods described in Nakanishi et al. U.S. Pat. No. 6,911,192, Nakanishi, "Pore Structure Control of Silica Gels Based on Phase Separation", *J. Porous. Mat.* 4:67, 1997, and Smått et. al. (Smått, et al. "Versatile Double-Templating Synthesis Route to Silica Monoliths Possessing a Multimodal Hierarchical Porosity", *Chem. Mater.* 15:2354, 2003), which are incorporated by reference herein for their teaching of templates and their method of preparation and use.

A carbon phase is then deposited in the porous template. The carbon phase can be deposited by infiltrating the template with a carbon precursor, such as a polymer precursor that can undergo thermally-initiated polymerization in situ within the template. Subsequent pyrolysis under an inert atmosphere converts the carbon precursor into carbon.

Methods for introducing carbon precursors into mesoporous silica templates and hierarchically porous silica templates are known in the art. See, e.g., Ryoo et al., "Ordered Mesoporous Carbons", *Adv. Mat.* 13:677, 2001, Lu et al., "Synthesis of Polyacrylonitrile-Based Ordered Mesoporous Carbon with Tunable Pore Structures", *Chem. Mater.* 16:100, 2004, Yang, et al. "Synthesis of replica mesostructures by the nanocasting strategy", *J. Mater. Chem.* 15:1217, 2005, and Hu et al., "Synthesis of Hierarchically Porous Carbon Monoliths with Highly Ordered Microstructure and Their Application in Rechargeable Lithium Batteries with High-Rate Capability", *Adv. Functional Mater.* 17:1873, 2007, which are incorporated herein for their teaching of carbon precursors, silica templates, and methods of using thereof. The resultant replica can be produced in one infiltration cycle and has very significant microporosity for most precursors used. The electrical conductivity of the replica is dependent upon the temperature, with temperatures of 800-1000° C. being necessary to produce highly conducting carbon.

Hollow, hierarchically porous carbon structures can be produced by increasing the viscosity of the infiltrating carbon precursor solution, and/or by increasing the rate at which the polymerization of the carbon precursor occurs. For example, hollow, porous carbon materials can be prepared by contacting a porous silica template, such as those known in the art, in particular a hierarchical porous silica template, and a polymerizable carbon precursor to form a mixture. This contacting step is performed such that the precursor does not infiltrate through the entire template and is referred to herein as partial infiltration. Then the mixture is heated to polymerize the precursor. Further heating is then performed to pyrolize the polymerized precursor, thereby producing a carbon porous material. These steps can be repeated with the same carbon precursor or with a different precursor. The formation of hollow, hierarchically porous structures can also be influenced by other parameters during this process, including pressure and template conditioning, for example humidity. For example, performing these steps at ambient pressure in combination with conditioning of the template (e.g., by controlling humidity) and/or varying the depth of carbon precursor solution infiltration might impact whether hollow hierarchically porous structures are obtained.

In these methods, particular infiltration can be accomplished by varying the time of contact, rate of polymerization, and viscosity of the precursor. The carbon precursor can be of increased viscosity so that it does not penetrate as far or as quickly as a low viscosity precursor. Specifying the exact viscosity of the carbon precursor is not possible since the desirable viscosity will depend on the size and type of template, the type of carbon precursor (which affects the rate of polymerization), the time the precursor is contacted with the template, and the desired level of infiltration. More viscous precursors allowed to contact the template for a longer period of time can produce similar structures as a less viscous precursor allowed to contact the template for a shorter period of time. Thus, the practitioner can determine a sufficient viscosity for a given precursor by simple experimentation, raising or lowering the viscosity or time of contact with the template as needed to obtain the desired level of infiltration. If more viscous precursors are needed, additives such as sugars, alcohols, glycols, and alkanes can be added. Other suitable methods for increasing the viscosity include allowing the carbon precursor to undergo some polymerization prior to introduction to the hierarchically porous silica template.

Further, the rate of polymerization of the precursor can be varied to provide a desired level of infiltration. More rapid polymerization means that the polymerizable carbon precursor would not infiltrate as far as a slower polymerization rate. Suitable methods for increasing the rate of the polymerization of the precursor prior to introduction to the porous template include, but are not limited to addition of crosslinking agents or polymerization initiators.

The carbon precursor can be for example, furfuryl alcohol, poly(furfuryl alcohol), formaldehyde, resorcinol, phenol, 1,2,3-trihydroxybenzene, 1,5-dihydroxynaphthalene, polyvinyl chloride-acrylate terpolymer, phenol resin, acrylonitrile-methyl methacrylate copolymer, polyimide, polypyrrolone, polyaromatic resin, polydivinylbenzene, sucrose, or mixtures thereof. Further examples of suitable carbon precursors are disclosed in Lu et al. chapters 2 and 3, *Nanocasting: A Versatile Strategy for Creating Nanostructured Porous Materials*; Royal Society of Chemistry: Cambridge, 2010, which is incorporated by reference herein for its teachings of carbon precursors, templates and nanocasting techniques.

Once a carbon phase has been deposited in the template, the template material can be removed to produce a hierarchically porous carbon material. The use of silica templates allows for the use of well defined chemistry to remove the template. For example, the porous material can be immersed in concentrated aqueous hydroxide solution at from about 25° C. to about 110° C. For example, the material can be immersed for a period of about 4 to about 12 hours in 1-3 M aqueous sodium or potassium hydroxide solution. Alternatively, the material can be immersed in hydrofluoric acid.

Other methods of making suitable hierarchically porous carbon monoliths include the use of mixtures carbon precursors and block copolymers, where the polymerization of the carbon precursor is carried out at low pH (<2) as disclosed in U.S. Pat. No. 8,114,510 to Dai, et al. See also U.S. Pat. No. 7,449,165 to Dai, et al. and U.S. Patent Application Publication No. US 2006/0057051 to Dai, et al. Suitable hierarchically porous carbon monoliths can also be made by the method disclosed by Hao et al. G.-P. Hao; W.-C. Li; S. Wang; G.-H. Wang; L. Qi; A.-H. Lu "Lysine-assisted rapid synthesis of crack-free hierarchical carbon monoliths with a hexagonal array of mesopores", *Carbon* 2011, 49, 3762-3772, which uses less acidic solutions. Suitable hierarchically porous carbon monoliths can also be made by the method disclosed by Yuang et al. Y. Huang; H. Cai; D. Feng; D. Gu; Y. Deng; B. Tu; H. Wang; P. A. Webley; D. Zhao "One-step hydrothermal synthesis of ordered mesostructured carbonaceous monoliths with hierarchical porosities", *Chem. Comm.* 2008, 2641-2643.

Suitable hierarchically porous carbon monoliths can also be made by using a method reported by Drisko et al. G. L. Drisko; A. e. Zelcer; V. Luca; R. A. Caruso; G. J. de A. A. Soler-Illia "One-Pot Synthesis of Hierarchically Structured Ceramic Monoliths with Adjustable Porosity", *Chem. Mater.* 2010, 22, 4379-4385. When this method is used to form silica monoliths the silica can be removed as discussed above leaving a hierarchically porous carbon monolith. The porous carbon material is then contacted with a composition comprising a metal salt. The carbon material is contacted with the metal salt such that the metal salt infiltrates into the porous carbon material.

The metal salt can be used in solution, hydrate or solvate form, or neat. When using a metal salt hydrate, solvate or neat salt, infiltration can be accomplished by contacting the porous template with the metal salt at above the salt's melt temperature, but below the salt's decomposition temperature. Alternatively, the metal salt can be part of a solution, i.e., the composition can comprise the metal salt and a solvent. For convenience, reference to the "metal salt" means either a neat metal salt, metal salt hydrate, metal salt solvate, or a metal salt solution, unless the context clearly refers to one or the other. Contacting the metal salt with the porous template can be performed by, for example, adding the porous template to the metal salt or by adding the metal salt solution to the porous template. Contacting can also be performed by slowly mixing one component with the other or by drop-wise addition of one component into the other. Agitation (e.g., stirring, shaking, or ultrasonic agitation) can be used to facilitate the contacting of the metal salt with the porous template.

The metal salts can comprise, for example, a transition metal, a lanthanide metal, or combinations thereof. In some embodiments, an additional metal, such as an alkaline metal, an alkaline earth metal, or a combination thereof, can also be present. In some cases, the metal salt comprises a metal selected from the group consisting of Ti, V, Cr, Mn, Fe, Co, Ni, Cu, Zr, Nb, Mo, Tc, Ru, Rh, Pd, Ag, Hf, Ta, W, Re, Os, Ir, Pt, Au, La, Ce, Pr, Nd, Pm, Sm, Eu, Gd, Tb, Dy, Ho, Er, Tm, Yb, and combinations thereof.

The counterion of the metal salt can be a nitrate, acetate, sulfate, or chloride. Other suitable counterions include organic or inorganic ions, such as carbonate, bromide, iodide, phosphate, sulfite, phosphite, nitrite, and combinations thereof. Metal salts suitable for use herein can be readily obtained from commercial suppliers or synthesized by methods known in the art. Similarly metal salt hydrates and metal salt solutions can be prepared by methods known in the art or obtained from commercial sources.

Metal salts for use herein have a decomposition temperature and a melting temperature. When using a composition comprising the metal salt hydrate, solvate, or neat metal salt the composition is heated above the melt temperature of the metal salt, but below the decomposition temperature of the metal salt.

When using a composition comprising a metal salt and a solvent, the solvent can be any suitable solvent that dissolves the particular metal salt being used. In certain aspects, water is used as the solvent. Other aqueous solvents can be used, such as water/organic solvent mixtures. Suitable water/organic solvent mixtures contain water and an organic solvent that is at least partially miscible with water. For example, as aqueous alcohols, aqueous polyols, aqueous carboxylic acids, aqueous esters, aqueous aldehydes, aqueous ketones, and the like can be used. In other examples, carboxylic acids, alcohols, polyols, ketones, or aldehydes can be used. In these embodiments, the solvent can optionally also act as the reducing agent.

When a solution of a metal salt is used, the weight or molar ratio of metal salt to solvent can be from about 1:1000 to about 10:1. For example, the weight ratio of metal salt to solution can be from about 1:1000, 1:750, 1:500, 1:250, 1:200, 1:150, 1:100, 1:75, 1:50, 1:40, 1:30, 1:25, 1:20, 1:15, 1:10, 2:10, 3:10, 4:10, 5:10, 6:10, 7:10, 8:10, 9:10, 10:9, 10:8, 10:7, 10:6, 10:5, 10:4, 10:3, 10:2, 10:1, or 1:1. In other examples, the molar ratio of metal salt to solution can be from about 1:1000, 1:750, 1:500, 1:250, 1:200, 1:150, 1:100, 1:75, 1:50, 1:40, 1:30, 1:25, 1:20, 1:15, 1:10, 2:10, 3:10, 4:10, 5:10, 6:10, 7:10, 8:10, 9:10, 10:9, 10:8, 10:7, 10:6, 10:5, 10:4, 10:3, 10:2, 10:1, or 1:1. A neat metal salt can be used as well, i.e., where there is no solvent. Further, metal salt hydrates and solvates can also be used. Such hydrates or solvates typically contain from 1 to 10 water or solvent molecules per metal center.

The porous carbon material is generally contacted with a composition comprising a metal salt at reduced pressure. The use of vacuum (e.g., from at or below about 1 Torr) to remove all air from the template and dissolved gases from the metal salt solution can produce an even spatial distribution of the metal salt and, consequently, metal and/or metal nanoparticles throughout the porous carbon template. For example, the pressure can be at or below about 100 Torr, 50 Torr, 10 Torr, 5 Torr, 1 Torr, 0.1 Torr, $10^{-2}$ Torr, $10^{-3}$ Torr, $10^{-4}$ Torr, $10^{-5}$ Torr, or $10^{-6}$ Torr, where any of the stated values can form an upper or lower endpoint of a range. The use of reduced pressure therefore allows the metal salt to completely infiltrate the macro-, meso-, and/or micropores of the porous template. Increasing the time of contact and reducing the temperature during contact can also be used to achieve complete infiltration of the metal salt into the porous template.

Once the desired spatial distribution of the metal salt in the porous template is attained, the metal salt is then reacted to form discrete nanoparticles that are evenly deposited on the carbon phase. Methods of reacting metal salts to form metal and/or metal oxide nanoparticles are known in the art. For example, the metal salt can be reduced by contacting the metal salt with a reducing agent, heating the metal salt to above the decomposition temperature of the metal salt, or combinations thereof. In some cases, the metal salt is reacted with a gas; however, the metal salt may also be reacted with, for example, a supercritical fluid.

The metal salt can be reacted by heating the metal salt to above the decomposition temperature of the metal salt. Heating can be conducted under a reducing or an inert atmosphere (e.g., under helium, nitrogen, argon, or combinations thereof).

The metal salt can be reacted by heating the metal salt in the presence of a reducing agent. The reducing agent can be added to the mixture by any method known in the art or described herein. Suitable reducing agents include hydrogen gas, alcohols (e.g., methanol, ethanol), polyols, polyethers (e.g., ethylene glycol), carboxylic acids (e.g., acetic acid), aldehydes, hydrazine, hydrides, ketones, boranes, and the like. In some embodiments, the reducing agent is a gas.

The metal salt can be reacted by contacting the metal salt with a reducing agent in the absence of heating. The reducing agent can be added to the mixture by any method known in the art or described herein. Suitable reducing agents include hydrogen gas, alcohols (e.g., methanol, ethanol), polyols, polyethers (e.g., ethylene glycol), carboxylic acids (e.g., acetic acid), aldehydes, hydrazine, hydrides, ketones, boranes, and the like. In some embodiments, the reducing agent is a gas.

Metal oxide nanoparticles can be formed by contacting the metal salt (and/or metal nanoparticles formed by reduction of a metal salt) with an oxidizing agent, such as an oxidizing atmosphere (e.g., oxygen, air, $CO_2$, or combinations thereof). In some embodiments, the oxidizing agent is a gas.

Following reaction of the metal salt, the hierarchically porous material can be cooled under nitrogen, and stored under nitrogen or degassed water or similar solvent. This can prevent reaction of the metal nanoparticles with ambient oxygen, if desired.

Applications

The hierarchically porous materials described above can be used as heterogenous catalysts. The hierarchically porous materials described herein are suitable for use in a wide variety of reactions including, but not limited to, oxidation reactions, reduction reactions, and cross-coupling reactions. For example, the hierarchically porous materials can be used to catalyze carbon-carbon bond forming reactions, the hydrogenation of carbon-carbon and carbon-heteroatom pi bonds (alkenes, alkynes, nitriles, imines, carbonyls, etc.), the reduction of carbon-nitrogen or carbon-oxygen pi bonds to give alcohols and amines, Fischer-Tropsch type chemistry to make hydrocarbons from $CO/H_2$, hydrogenolysis of ethers to alcohols, hydrogenolysis of amines to less-substituted amines, hydrogen production from biomass, Pauson-Khand reactions (alkyne+alkene+CO to give cyclopentanones), and catalytic dehalogenation reaction (e.g., dechlorination of aromatic compounds).

The hierarchically porous materials can also be used to catalyze oxidation reactions (e.g., to catalyze the oxidation of alcohols and aldehydes; to catalyze the oxidative carbonylation of alcohols and amines to carbonates, carbamates or ureas; and to catalyze Wacker oxidations).

The utility of the hierarchically porous materials for a particular catalytic application will depend on several factors, including the nature of the inorganic nanoparticles deposited within the pores of the hierarchically porous carbon body, as well as the morphology of the hierarchically porous material. Appropriate hierarchically porous materials for a particular catalytic application can be selected in view of the type of reaction being performed. For example, in some embodiments, the hierarchically porous materials selected for a particular catalytic application contains inorganic nanoparticles of similar composition (e.g., containing the same metal, containing a different metal that has similar catalytic activity) as catalysts typically employed for the particular catalytic application. For example, hierarchically porous nanoparticles comprising Pd-nanoparticles can be used to catalyze reactions currently catalyzed via Pd-catalysts such as, for example, Sonogashira-type cross-coupling reactions.

Reactions are typically performed using established procedures for a particular type of reaction; however, the traditional catalyst is replaced with an appropriate hierarchically porous material, as described herein. The reactants are contacted with the catalyst under suitable conditions, including time, temperature, and pressure, for the reaction to proceed, as desired. Solvents and co-solvents can optionally be present in the reaction mixture. In some instances, the reaction mixture can be contacted by one or more additional reagents, if required or desired. For example, in the case of a Sonogashira-type cross-coupling reaction, an amine base, such as triethylamine, piperidine, or Hunig's base, can be added to the reaction mixture. Examples of additional reagents that can be added include hydrogen, an acid (e.g., formic acids or salts thereof), oxygen, a base, hydrogen peroxide, an organic peroxide, or combinations thereof.

In some embodiments, hierarchically porous materials containing metal nanoparticles can be used to catalyze cross-coupling reactions (e.g., carbon-carbon bond forming reactions). For example, these materials can be utilized to catalyze bond-forming reactions between an organic halide and a suitable nucleophile.

Hierarchically porous material containing metal nanoparticles can be used to catalyze Heck coupling reactions (also known as Mizoroki-Heck reactions). Generally, Heck reactions involve contacting an organohalide and an olefin with a suitable catalyst in the presence of a base. For example, the organohalide can be an unsaturated halide, such as an aryl or vinyl halide. Heck reactions can also be used to couple pseudohalides, such as triflates (OTf), with olefins. Heck reactions are known in the art. See, for example, Heck, R. F. and Nolley, J. P. *J. Am. Chem. Soc.* 90:5518 (1968); Heck, R. F. *Acc. Chem. Res.* 12:146 (1979); Beletskaya, I. P. and Cheprakov, A. V. *Chem. Rev.* 100:3009 (2000). In certain embodiments, a hierarchically porous material comprising Pd nanoparticles, Ni nanoparticles, Cu nanoparticles, or combinations thereof, is used to catalyze a Heck reaction.

Hierarchically porous material containing metal nanoparticles can be used to catalyze Suzuki coupling reactions. Generally, Suzuki reactions involve contacting an organohalide and an organoborane with a suitable catalyst in the presence of a base. For example, the organohalide can be an unsaturated halide, such as an aryl or vinyl halide. The organoborane can be an unsaturated boronic acid, such as an aryl- or vinyl-boronic acid. Boronic esters and organotrifluoroborate salts may be used instead of boronic acids. Suzuki reactions can also be used to couple pseudohalides, such as triflates (OTf), with organoboranes. Suzuki reactions are known in the art. See, for example, Miyaura, N. and Suzuki, A. *Chem. Rev.* 95:2457 (1995), Stanforth, S. P. *Tetrahedron* 54:263 (1998), Lipshutz, et al., Synthesis, 2989 (2005), and Lipshutz, et al., Organic Letters, 10, 4279 (2008). In certain embodiments, a hierarchically porous material comprising Pd nanoparticles, Ni nanoparticles, Cu nanoparticles, or combinations thereof, is used to catalyze a Suzuki reaction.

Hierarchically porous material containing metal nanoparticles can be used to catalyze Sonogashira coupling reactions. Generally, Sonogashira reactions involve contacting an organohalide and a terminal alkyne with a suitable catalyst or catalysts in the presence of a base. For example, the organohalide can be an unsaturated halide, such as an aryl or vinyl halide. Sonogashira reactions are known in the art. See, for example, Sonogashira, K. et al. *Tetrahedron Lett.* 4467 (1975); Sonogashira, K. *J. Organomet. Chem.* 653:46 (2002). In certain embodiments, a hierarchically porous material comprising Pd nanoparticles, Ni nanoparticles, Cu nanoparticles, or combinations thereof, is used to catalyze a Sonogashira reaction. In some embodiments, a hierarchically porous material comprising Pd nanoparticles is used to catalyze a Sonogashira reaction, and a copper co-catalyst is separately added to the reaction mixture.

Hierarchically porous material containing metal nanoparticles can be used to catalyze Hiyama coupling reactions. Generally, Hiyama reactions involve contacting an organohalide and an organosilane with a suitable catalyst in the presence of an activating agent, such as fluoride or hydroxide. For example, the organohalide can be an unsaturated halide, such as an aryl or vinyl halide. Hiyama reactions can also be used to couple pseudohalides, such as triflates (OTf), with organosilanes. Hiyama reactions are known in the art. See, for example, Hatanaka, Y. and Hiyama, T. *J. Org. Chem.* 53:918 (1988); and Hiyama T. and Hatanaka, Y. *Pure Appl. Chem.* 66:1471 (1994). In certain embodiments, a hierarchically porous material comprising Pd nanoparticles, Ni nanoparticles, or combinations thereof, is used to catalyze a Hiyama reaction.

Hierarchically porous material containing metal nanoparticles can be used to catalyze Negishi coupling reactions. Generally, Negishi reactions involve contacting an organohalide and an organozinc compound with a suitable catalyst. Negishi reactions can also be used to couple pseudohalides, such as triflates (OTf) and acetyloxy groups, with organozinc compounds. Negishi reactions are known in the art. See, for example, Negishi, E.-I. *Acc. Chem. Res.* 15:340 (1982); and Erdik, E. *Tetrahedron* 48:9577 (1992). In certain embodiments, a hierarchically porous material comprising Pd nanoparticles, Ni nanoparticles, or combinations thereof, is used to catalyze a Negishi reaction.

Hierarchically porous material containing metal nanoparticles can be used to catalyze Kumada coupling reactions. Generally, Kumada reactions involve contacting an organohalide and a Grignard reagent (e.g., a magnesium halide) with a suitable catalyst. Kumada reactions can also be used to couple pseudohalides, such as triflates (OTf) and tosylates, with Grignard reagents. Kumada reactions are known in the art. See, for example, Tamao, K. et al. *Bull. Chem. Soc. Jpn.* 49:1958 (1976); Kalinin, V. N. *Synthesis* 413 (1992); and Stanforth, S. P. *Tetrahedron* 54:263 (1998). In certain embodiments, a hierarchically porous material comprising Pd nanoparticles, Ni nanoparticles, or combinations thereof, is used to catalyze a Kumada reaction.

Hierarchically porous material containing metal nanoparticles can be used to catalyze Stille coupling reactions. Generally, Stille reactions involve contacting an organohalide and an organostannane with a suitable catalyst. For example, the organohalide can be an unsaturated halide, such as an aryl or vinyl halide. Stille reactions can also be used to couple pseudohalides, such as triflates (OTf) and tosylates, with organostannanes. Stille reactions are known in the art. See, for example, Milstein, D. and Stille, J. K. *J. Am. Chem. Soc.* 100:3636 (1978); Milstein, D. and Stille, J. K. *J. Am. Chem. Soc.* 101:4992 (1979); and Duncton, M. A. J. and Pattenden, G. *J. Chem. Soc.; Perkin Trans* 1 1235 (1999). In certain embodiments, a hierarchically porous material comprising Pd nanoparticles, Ni nanoparticles, Cu nanoparticles, or combinations thereof is used to catalyze a Stille reaction.

Hierarchically porous material containing metal nanoparticles can be used to catalyze Buchwald-Hartwig coupling reactions. Generally, Buchwald-Hartwig reactions involve contacting an organohalide and a heteroatom (e.g., N, O, S, P, Se, etc.) or enolate nucleophile with a suitable catalyst. For example, the organohalide can be an unsaturated halide, such as an aryl or vinyl halide. The heteroatom nucleophile can be, for example, an amine, an alcohol, or a thiol. Buchwald-Hartwig reactions are known in the art. See, for example, Paul, F. et al. *J. Am. Chem. Soc.* 116:5969 (1994); Guram, A. S. and Buchwald, S. L. *J. Am. Chem. Soc.* 116:7901 (1994); Wolfe, J. P. et al. *Acc. Chem. Res.* 31:805 (1998); and Hartwig, J. F. *Acc. Chem. Res.* 31:852 (1998). In certain embodiments, a hierarchically porous material comprising Pd nanoparticles, Ni nanoparticles, Cu nanoparticles, or combinations thereof, is used to catalyze a Buchwald-Hartwig reaction.

Hierarchically porous material containing metal nanoparticles can be used to catalyze Ullmann coupling reactions. Generally, Ullmann reactions involve contacting an organohalide with a suitable catalyst. For example, the organohalide can be an unsaturated halide, such as an aryl or vinyl halide. Ullmann reactions are known in the art. See, for example, Ullmann, F. *Justus Liebigs Ann. Chem.* 332:38 (1904); Fanta, P. E. *Synthesis* 9 (1974); Stark, L. M., et al. J. Org. Chem. 65:3227 (2000); and Belfield, K. D., et al. *J. Org. Chem.* 65:4475 (2000). In certain embodiments, a hierarchically porous material comprising Cu nanoparticles, Pd nanoparticles, Ni nanoparticles, or combinations thereof, is used to catalyze an Ullmann reaction.

Hierarchically porous material containing metal nanoparticles can be used to catalyze Fukuyama coupling reactions. Generally, Fukuyama reactions involve contacting an organozinc halide and a thioester with a suitable catalyst. Fukuyama reactions are known in the art. See, for example, Tokuyama, H. et al. *Tetrahedron Lett.* 39:3189 (1998). In certain embodiments, a hierarchically porous material comprising Pd nanoparticles, Ni nanoparticles, or combinations thereof is used to catalyze a Fukuyama reaction.

Hierarchically porous material containing metal nanoparticles can be used to catalyze the hydrogenation of carbon-carbon and carbon-heteroatom pi bonds (alkenes, alkynes, nitriles, imines, carbonyls, etc.). Catalytic hydrogenation reactions generally involve contacting a reagent to be hydrogenated (e.g., a compound containing a carbon-carbon and/or carbon-heteroatom pi bond) with hydrogen gas and a suitable catalyst. The reaction can carried out at different temperatures and pressures, depending upon the substrate and the activity of the catalyst. For example, the hydrogenation can be a catalytic conversion of a monoolefin to an alkane, a catalytic conversion of a diolefin to a monoolefin, a catalytic hydrogenation of an acetylene group, a catalytic hydrogenation of an aromatic ring, a catalytic hydrogenation of a heteroaromatic ring, a catalytic conversion of a nitro group to an amine, a catalytic conversion of a nitroso group to an amine group, a catalytic conversion of a hydrazone group to hydrazine group, a catalytic conversion of an imine group to an amine group, a catalytic conversion of a nitrile group to an amine group, a catalytic reductive alkylation, a catalytic reductive amination, a catalytic disproportionation reaction, or a catalytic Rosenmund reaction.

Hierarchically porous material containing metal nanoparticles can be used to catalyze hydrogenolysis reactions. Catalytic hydrogenolysis reactions generally involve contacting a reagent containing a carbon-carbon or carbon-heteroatom single bond to be cleaved with hydrogen gas or a hydrogen donor, such as an alcohol, polyol, or formic acid or salt thereof, and a suitable catalyst. The reaction can carried out at different temperatures and pressures, depending upon the substrate and the activity of the catalyst. For example, the hydrogenolysis can be a catalytic debenzylation reaction, a catalytic deallylation reaction, a catalytic carbon-oxygen bond cleavage, a catalytic carbon-nitrogen bond cleavage, or a catalytic decarbonylation.

Hierarchically porous materials can also be used to catalyze the oxidation of an alcohol. These reactions typically involve contacting a suitable compound containing an alcohol moiety with a catalyst in the presence of an oxidant, such as a ketone, air, or oxygen. Depending on the catalyst and reaction conditions, the alcohol can be oxidized, for example, to an aldehyde, ketone, or carboxylic acid.

Hierarchically porous materials can also be used to catalyze the reduction of a carboxylic acid to an alcohol. These reactions typically involve contacting a suitable compound containing a carboxylic acid moiety with a catalyst.

In certain embodiments, the hierarchically porous material comprises Pd nanoparticles, and the reaction is a Heck coupling, Suzuki coupling, Sonogashira coupling, Hiyama coupling, Negishi coupling, Kumada coupling, Stille coupling, Buchwald-Hartwig coupling, Fukuyama coupling, a catalytic conversion of a monoolefin to an alkane, a catalytic conversion of a diolefin to a monoolefin, a catalytic hydrogenation of an acetylene group, a catalytic hydrogenation of an aromatic ring, a catalytic hydrogenation of a heteroaromatic ring, a catalytic conversion of a nitro group to an amine, a catalytic conversion of a nitroso group to an amine group, a catalytic conversion of a hydrazone group to hydrazine group, a catalytic conversion of an imine group to an amine group, a catalytic conversion of a nitrile group to an amine group, a catalytic reductive alkylation, a catalytic reductive amination, a catalytic disproportionation reaction, a catalytic Rosenmund reaction, a catalytic debenzylation reaction, a catalytic deallylation reaction, a catalytic carbon-oxygen bond cleavage, a catalytic carbon-nitrogen bond cleavage, a catalytic decarbonylation, a catalytic oxidation of an alcohol, or a carboxylic acid to an alcohol.

In certain embodiments, the hierarchically porous material comprises Pt nanoparticles, and the reaction is a catalytic conversion of a monoolefin to an alkane, a catalytic hydrogenation of an aromatic ring, a catalytic conversion of a nitro group to an amine, a catalytic conversion of an aldehyde group to an alcohol, a catalytic conversion of a nitroso group to an amine group, a catalytic conversion of a hydrazone group to hydrazine group, a catalytic conversion of aromatic nitro compound to a paranitrophenol, a catalytic conversion of an imine group to an amine group, a catalytic conversion of a nitrile group to an amine group, a catalytic reductive alkylation, or a catalytic reductive amination.

In certain embodiments, the hierarchically porous material comprises Ru nanoparticles, and the reaction is a catalytic conversion of a monoolefin to an alkane, a catalytic hydrogenation of an aromatic ring, a catalytic hydrogenation of a heteroaromatic ring, a catalytic conversion of an aldehyde group to an alcohol, a catalytic conversion of a ketone to an alcohol.

In certain embodiments, the hierarchically porous material comprises Rh nanoparticles, and the reaction is a catalytic conversion of a monoolefin to an alkane, a catalytic hydrogenation of an aromatic ring, a catalytic hydrogenation of a heteroaromatic ring, a catalytic conversion of a nitroso group to an amine group, a catalytic conversion of a nitrile group to an amine group.

The hierarchically porous materials described herein can offer advantages over traditional heterogeneous catalysts given their high surface area, which would aid efficiency, and their monolithic structure, which would simplify separation of the catalyst and make continuous flow reactions an option.

The hierarchically porous materials described herein can also be used in other applications, including filtration and separation.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

Silica monoliths were produced using the methods described by U.S. Pat. No. 6,911,192 to Nakanishi; Nakanishi, K. "Pore Structure Control of Silica Gels Based on Phase Separation", *J. Porous. Mat.* 4:67-112 (1997); and Smått, J.-K., et al. "Versatile Double-Templating Synthesis Route to Silica Monoliths Possessing a Multimodal Hierarchical Porosity", *Chem. Mater.* 15:2354-2361 (2003). The carbon replicas used in these examples were produced either from a silica template using methods described by Lu, A.-H., et al. "Combined Surface and Volume Templating of Highly Porous Nanocast Carbon Monoliths", *Adv. Funct. Mater.* 15:865-871 (2005), or according to methods described by Hao et. al. "Lysine-assisted rapid synthesis of crack-free hierarchical carbon monoliths with a hexagonal array of mesopores", Carbon, 49:3762-3772 (2011).

Example 1

Formation of a Carbon Monolith Loaded with 5% Pd Nanoparticles

Carbon monoliths were produced according to methods described by Lu, A.-H., et al. "Combined Surface and Volume Templating of Highly Porous Nanocast Carbon Monoliths", *Adv. Funct. Mater.* 15:865-871 (2005). These carbon monoliths were activated by soaking in 10 mL of 2 M nitric acid per gram of carbon at 80° C. for 2 hours. Activated carbon monoliths were rinsed with deionized water until the pH reached 7. Activated carbon monoliths were then dried at 90° C. under vacuum overnight.

A solution comprising 0.03046 g of $Pd(NH_3)_4Cl_2.H_2O$ per 1 mL of deionized water was prepared. Carbon monoliths were placed under vacuum for 20 minutes, and filled with the Pd salt solution. Excess solution was removed from the outside of the monoliths and they were dried for 1 hour under nitrogen flow at 150° C. and cooled to room temperature. Then the monoliths were heated to 100° C. at a rate of 1° C./min and held at 100° C. for 4 hours while flowing 5% hydrogen in nitrogen. After 4 hours, the gas was changed to 100% nitrogen and the monoliths were allowed to cool to room temperature. This resulted in an activated carbon monolith loaded with 5% Pd metal by weight.

Electron microscopy confirmed the presence of well dispersed Pd nanoparticles having an average diameter of 7 nm, as shown in FIG. 1. Energy Dispersive X-ray Spectroscopy confirmed the presence of only Pd and carbon.

Example 2

Formation of a Carbon Monolith Loaded with 1% Pd Nanoparticles

Carbon monoliths were produced according to methods described by Lu, A.-H., et al. "Combined Surface and Volume Templating of Highly Porous Nanocast Carbon Monoliths", *Adv. Funct. Mater.* 15:865-871 (2005). These carbon monoliths were activated by soaking in 10 mL of 2 M nitric acid per gram of carbon at 80° C. for 2 hours. Activated carbon monoliths were rinsed with deionized water until the pH reached 7. Activated carbon monoliths were then dried at 90° C. under vacuum overnight.

A solution comprising 0.0061 g of $Pd(NH_3)_4Cl_2.H_2O$ per 1 mL of deionized water was prepared. Carbon monoliths were dried under vacuum for 20 minutes and filled with the Pd salt solution. Excess solution was removed from the outside of the monoliths the following day and the monoliths were heated at 150° C. for 3 hours while flowing 5% hydrogen in nitrogen. After 3 hours, the gas was changed to 100% nitrogen and the monoliths were allowed to cool to room temperature. This resulted in an activated carbon monolith loaded with 1% Pd metal by weight.

Figure 2:
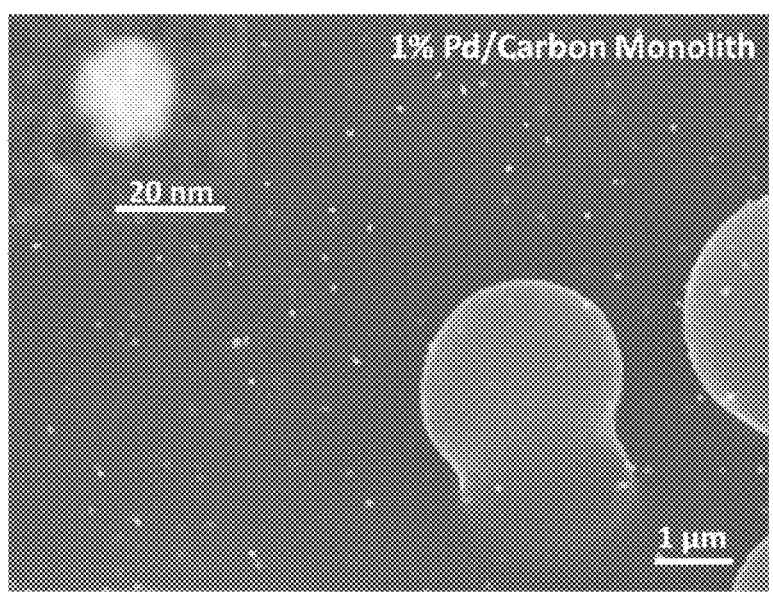
FIG. 2 is an SEM image of Pd nanoparticles dispersed in a hierarchically porous carbon monolith (scale bar=1 µM). The inset image shows an enlarged view of a single nanoparticle (scale bar=20 nm). The carbon monolith was loaded with 1% Pd by weight nanoparticles. The SEM image confirmed the presence of well dispersed Pd nanoparticles having an average diameter of 15 nm within the hierarchically porous carbon monolith.

Electron microscopy confirmed the presence of well dispersed Pd nanoparticles with diameters ranging from 5 to 12.5 nm having an average diameter of 7.5 nm, as shown in FIG. 2. Energy Dispersive X-ray Spectroscopy confirmed the presence of only Pd and carbon. The resulting specific surface area of the Pd nanoparticles was 1000 $m^2/g$.

Example 3

Formation of a Carbon Monolith Loaded with 1% Pd Nanoparticles

Carbon monoliths were produced according to methods described by Hao et. al. "Lysine-assisted rapid synthesis of crack-free hierarchical carbon monoliths with a hexagonal array of mesopores", Carbon, 49:3762-3772 (2011). Specifically, 3.0 grams of resorcinol, 0.29 grams of lysine, 1.26 grams of 35,000 molecular polyethylene oxide, and 2.44 g of formaldehyde were added to a mixture of 8.8 g of water and 9.0 grams of ethanol. After 10 minutes of stirring, the solution was pipetted into 2×2 cm square wells which were placed in a sealed container with 8.8 grams of water and 9.0 grams of ethanol and heated to 90° C. for 2 hours. The samples were then removed from the wells, and dried overnight at 50° C. The samples were then pyrolyzed under flowing nitrogen gas by heating to 400° C. at a ramp of 2° C./min, incubating at 400° C. for one hour, then heating to 800° C. at a 5° C./min ramp, incubating at 800° C. for 2 hours, and then cooling to room temperature.

1.5 g of these carbon monoliths were activated by soaking in 10 mL of 2 M nitric acid per gram of carbon at 80° C. for 2 hours. The activated carbon monoliths were rinsed with deionized water until the pH reached 7. The activated carbon monoliths were then dried at 90° C. under vacuum overnight.

A solution comprising 0.0061 g of $Pd(NH_3)_4Cl_2 \cdot H_2O$ per 1 mL of deionized water was prepared. Carbon monoliths were dried under vacuum for 20 minutes and filled with the Pd salt solution. Excess solution was removed from the outside of the monoliths the following day and the monoliths were heated at 150° C. for 3 hours while flowing 5% hydrogen in nitrogen. After 3 hours, the gas was changed to 100% nitrogen and the monoliths were allowed to cool to room temperature. This resulted in an activated carbon monolith loaded with 1% Pd metal by weight.

Electron microscopy confirmed the presence of well dispersed Pd nanoparticles with diameters ranging from 12.5 to 150 nm having an average diameter of 94 nm. Energy Dispersive X-ray Spectroscopy confirmed the presence of only Pd and carbon.

Example 4

Formation of a Carbon Monolith Loaded with 1% Pt Nanoparticles

Carbon monoliths were produced according to methods taught by Hao et. al. "Lysine-assisted rapid synthesis of crack-free hierarchical carbon monoliths with a hexagonal array of mesopores", Carbon, 49:3762-3772 (2011). 1.41 g of these carbon monoliths were activated by soaking in 10 mL of 2 M nitric acid per gram of carbon at 80° C. for 18 hours. The activated carbon monoliths were rinsed with deionized water until the pH reached 7. The activated carbon monoliths were then dried at 90° C. under vacuum overnight.

A solution comprising 0.0129 g of $H_2Cl_6Pt6H_2O$ per 1 mL of deionized water was prepared. Carbon monoliths were dried under vacuum for 120 minutes and filled with the Pt salt solution. Excess solution was removed from the outside of the monoliths the following day and the monoliths were heated at 150° C. for 3 hours while flowing 5% hydrogen in nitrogen. After 3 hours, the gas was changed to 100% nitrogen and the monoliths were allowed to cool to room temperature. This resulted in an activated carbon monolith loaded with 1% Pt metal by weight.

Electron microscopy confirmed the presence of well dispersed Pt-containing nanoparticles with diameters ranging from 5.5 to 22 nm having an average diameter of 14 nm. Energy Dispersive X-ray Spectroscopy confirmed the presence of carbon and Pt and chlorine in an approximate 1:2 ratio. The Energy Dispersive X-ray Spectroscopy result was consistent incomplete reduction of the platinum salt. Higher heating temperatures, such as those described in the examples below, could be used to form Pt nanoparticles dispersed within the carbon monolith.

Example 5

Formation of a Carbon Monolith Loaded with 1% Ru Nanoparticles

Carbon monoliths were produced according to methods taught by Hao et. al. "Lysine-assisted rapid synthesis of crack-free hierarchical carbon monoliths with a hexagonal array of mesopores", Carbon, 49:3762-3772 (2011). 1.4 g of these carbon monoliths were activated by soaking in 100 mL of 2 M nitric acid per gram of carbon at 80° C. for 18 hours. The activated carbon monoliths were rinsed with deionized water until the pH reached 7. The activated carbon monoliths were then dried at 90° C. under vacuum overnight.

A solution comprising 0.00515 g of $RuCl_3$ hydrate per 1 mL of deionized water was prepared. Carbon monoliths were dried under vacuum for 120 minutes and filled with the Ru salt solution. Excess solution was removed from the outside of the monoliths the following day and the monoliths were heated at 150° C. for 1 hours while flowing nitrogen gas. After cooling to room temperature the carbon monoliths were heated under flowing 5% hydrogen in nitrogen gas to 300° C. in two hours and then kept at 300° C. for 4 hours. The gas was changed to 100% nitrogen and the monoliths were allowed to cool to room temperature. This resulted in an activated carbon monolith loaded with 1% Ru metal by weight.

Electron microscopy confirmed the presence of well dispersed Ru nanoparticles having an average diameter of 15 nm. Energy Dispersive X-ray Spectroscopy confirmed the presence of only Ru and carbon.

Example 6

Formation of a Carbon Monolith Loaded with 1% Rh Nanoparticles

Carbon monoliths were produced according to methods taught by Hao et. al. "Lysine-assisted rapid synthesis of crack-free hierarchical carbon monoliths with a hexagonal array of mesopores", Carbon, 49:3762-3772 (2011). 1.4 g of these carbon monoliths were activated by soaking in 10 mL of 2 M nitric acid per gram of carbon at 80° C. for 18 hours. The activated carbon monoliths were rinsed with deionized water until the pH reached 7. The activated carbon monoliths were then dried at 90° C. under vacuum overnight.

A solution comprising 0.00520 g of $RhCl_3$ per 1 mL of deionized water was prepared. Carbon monoliths were dried under vacuum for 120 minutes and filled with the Rh salt solution. Excess solution was removed from the outside of the monoliths the following day and the monoliths were heated at 150° C. for 1 hours while flowing nitrogen gas. After cooling to room temperature the carbon monoliths were heated under flowing 5% hydrogen in nitrogen gas to 300° C. in two hours and then kept at 300° C. for 4 hours. The gas was changed to 100% nitrogen and the monoliths were allowed to cool to room temperature. This resulted in an activated carbon monolith loaded with 1% Rh metal by weight.

Electron microscopy confirmed the presence of well dispersed Rh nanoparticles having an average diameter of 15 nm. Energy Dispersive X-ray Spectroscopy confirmed the presence of only Rh and carbon.

Example 7

Formation of a Carbon Monolith Loaded with 1% Pt Nanoparticles

Carbon monoliths were produced according to methods taught by Lu, A.-H., et al. "Combined Surface and Volume Templating of Highly Porous Nanocast Carbon Monoliths", *Adv. Funct. Mater.* 15:865-871 (2005). These carbon monoliths were activated by soaking in 10 mL of 2 M nitric acid per gram of carbon at 80° C. for 24 hours. These carbon monoliths were further activated by soaking in 100 mL of 2 M nitric acid per gram of carbon at 80° C. for 24 hours. Activated carbon monoliths were rinsed with deionized water until the pH reached 7. Activated carbon monoliths were then dried at 90° C. under vacuum overnight.

A solution comprising 0.0129 g of H$_2$Cl$_6$Pt6H$_2$O per 1 mL of deionized water was prepared. Carbon monoliths (0.243 g) were dried under vacuum for 120 minutes and filled with the Pt salt solution. Excess solution was removed from the outside of the monoliths the following day and the monoliths were heated at 150° C. for 1 hour while flowing nitrogen. After cooling to room temperature the carbon monoliths were heated under flowing 5% hydrogen in nitrogen gas to 300° C. in two hours and then kept at 300° C. for 4 hours. The gas was changed to 100% nitrogen and the monoliths were allowed to cool to room temperature. This resulted in an activated carbon monolith loaded with 1% Pt metal by weight.

Electron microscopy confirmed the presence of well dispersed Pt nanoparticles, typically of 15-25 nm in diameter. Energy Dispersive X-ray Spectroscopy confirmed the presence of Pt and carbon. Some residual chlorine was detected by Energy Dispersive X-ray Spectroscopy; however, the chlorine detected was present at significantly lower level than the platinum, consistent with the complete reduction to platinum metal.

Example 8

Formation of a Carbon Monolith Loaded with 1% Rh Nanoparticles

Carbon monoliths were produced according to methods taught by Lu, A.-H., et al. "Combined Surface and Volume Templating of Highly Porous Nanocast Carbon Monoliths", *Adv. Funct. Mater.* 15:865-871 (2005). These carbon monolithes were activated by soaking in 10 mL of 2 M nitric acid per gram of carbon at 80° C. for 24 hours. Activated carbon monoliths were rinsed with deionized water until the pH reached 7. Activated carbon monoliths were then dried at 90° C. under vacuum overnight.

A solution comprising 0.00520 g of RhCl$_3$ per 1 mL of deionized water was prepared. Carbon monoliths (0.43 g) were dried under vacuum for 120 minutes and filled with the Rh salt solution. Excess solution was removed from the outside of the monoliths the following day and the monoliths were heated at 150° C. for 1 hours while flowing nitrogen gas. After cooling to room temperature the carbon monoliths were heated under flowing 5% hydrogen in nitrogen gas to 300° C. in two hours and then kept at 300° C. for 4 hours. The gas was changed to 100% nitrogen and the monoliths were allowed to cool to room temperature. This resulted in an activated carbon monolith loaded with 1% Rh metal by weight.

Electron microscopy confirmed the presence of well dispersed Rh nanoparticles with diameters ranging from 10.5 to 34 nm having an average diameter of 20 nm. Energy Dispersive X-ray Spectroscopy confirmed the presence of only Rh and carbon. Some residual chlorine was detected by Energy Dispersive X-ray Spectroscopy; however, the chlorine detected was present at significantly lower level than the rhodium, consistent with the complete reduction to rhodium metal.

Example 9

Formation of a Carbon Monolith Loaded with 1% Ru Nanoparticles

Carbon monoliths were produced according to methods taught by Lu, A.-H., et al. "Combined Surface and Volume Templating of Highly Porous Nanocast Carbon Monoliths", *Adv. Funct. Mater.* 15:865-871 (2005). These carbon monoliths were activated by soaking in 100 mL of 2 M nitric acid per gram of carbon at 80° C. for 24 hours. Activated carbon monoliths were rinsed with deionized water until the pH reached 7. These carbon monoliths were further activated by soaking in 100 mL of 2 M nitric acid per gram of carbon at 80° C. for 24 hours. Activated carbon monoliths were rinsed with deionized water until the pH reached 7. Activated carbon monoliths were then dried at 90° C. under vacuum overnight.

A solution comprising 0.00515 g of RuCl$_3$ hydrate per 1 mL of deionized water was prepared. Carbon monoliths (0.829 g) were dried under vacuum for 120 minutes and filled with the Ru salt solution. Excess solution was removed from the outside of the monoliths the following day and the monoliths were heated at 150° C. for 1 hours while flowing nitrogen gas. After cooling to room temperature the carbon monoliths were heated under flowing 5% hydrogen in nitrogen gas to 300° C. in two hours and then kept at 300° C. for 4 hours. The gas was changed to 100% nitrogen and the monoliths were allowed to cool to room temperature. This resulted in an activated carbon monolith loaded with 1% Ru metal by weight.

Electron microscopy confirmed the presence of well dispersed Ru nanoparticles. Energy Dispersive X-ray Spectroscopy confirmed the presence of only Ru and carbon. Some residual chlorine was detected by Energy Dispersive X-ray Spectroscopy; however, the chlorine detected was present at significantly lower level than the ruthenium, consistent with the complete reduction to ruthenium metal.

Example 10

Heck Reactions Using a 1% Pd/C Monolith as a Catalyst

The Pd/C monolith (42 mg of a 1% Pd/C monolith, 2 mol % Pd) prepared according to the method described in Example 2 was added to a 1 dram glass vial in air followed by iodobenzene (28 μL, 0.25 mmol), n-butylacrylate (54 μL, 0.375 mmol), ethyldiisopropylamine (1.5 equiv, 0.375 mmol, 65 μL) and 1 mL DMF. The vial was sealed under air with a rubber septum cap and placed in an oil bath preheated to 80° C. for 24 hours. After the allotted time, the reaction mixture was dissolved in ethyl acetate. Gas chromatographic analysis indicated a 71% yield of (E)-n-butyl cinnamate.

4-Iodobenzonitrile (57 mg, 0.25 mmol) and n-butylacrylate (54 μL, 0.375 mmol) were coupled using the procedure described above, except the reaction was performed at 50° C., to give 100% conversion to (E)-n-butyl 3-(4-cyanophenyl) acrylate by GC analysis.

4-Iodoanisole (58 mg, 0.25 mmol) and n-butylacrylate (54 μL, 0.375 mmol) were coupled using the procedure described above to give 74% conversion to (E)-n-butyl 3-(4-methoxyphenyl)acrylate by GC analysis.

2-Iodotoluene (32 μL, 0.25 mmol) and n-butylacrylate (54 μL, 0.375 mmol) were coupled using the procedure described above to give 83% conversion to (E)-n-butyl 3-(2-methylphenyl)acrylate by GC analysis.

Iodobenzene (32 μL, 0.25 mmol) and styrene (43 μL, 0.375 mmol) were coupled using the procedure described above to give 81% conversion to (E)-stilbene by GC analysis.

4-Iodobenzonitrile (57 mg, 0.25 mmol) and styrene (43 μL, 0.375 mmol) were coupled using the procedure described above to give 63% conversion to (E)-4-cyanostilbene by GC analysis.

4-Iodoanisole (58 mg, 0.25 mmol) and styrene (43 μL, 0.375 mmol) were coupled using the procedure described above, but using triethylamine (0.375 mmol, 52 μL) in place of ethyldiisopropylamine, to give 100% conversion to (E)-4-methoxystilbene by GC analysis.

2-Iodotoluene (32 μL, 0.25 mmol) and styrene (43 μL, 0.375 mmol) were coupled using the procedure described above to give 57% conversion to (E)-2-methylstilbene by GC analysis.

Catalytic Activity Over Multiple Reaction Cycles

Iodobenzene (0.25 mmol) and n-butyl acrylate (1.5 equiv) were reacted as described above. After the reaction was complete, an aliquot was removed from the reaction and dissolved in ethyl acetate for GC analysis. New portions of iodobenzene (0.25 mmol), n-butyl acrylate (1.5 equiv), and $^i$Pr$_2$NEt (1.5 equiv) were added under air. A total of three reaction cycles were performed in this way with the same Pd/C monolith. GC analysis of the reaction mixture after each cycle showed 100% conversion of iodobenzene to (E)-n-butyl cinnamate.

Example 11

Comparison of Pd/C Monoliths in the Heck Coupling

Figure 3:
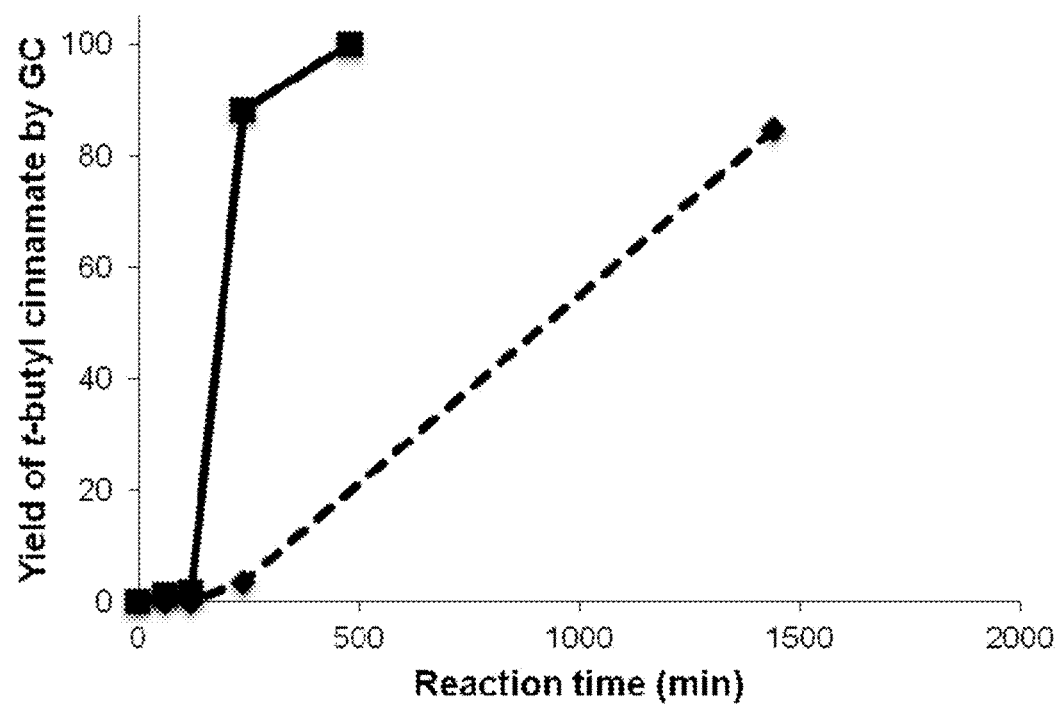
FIG. 3 is a plot of the percent conversion of iodobenzene and t-butyl acrylate to t-butyl cinnamate as a function of reaction time (in minutes) using the catalyst prepared in Example 2 (solid trace) and the catalyst prepared in Example 3 (dashed trace).

Pd/C monoliths prepared as described in Examples 2 and 3 above (2 mol % Pd) were added to a 1 dram glass vial in air followed by iodobenzene (28 μL, 0.25 mmol), t-butyl acrylate (54 μL, 0.375 mmol), ethyldiisopropylamine (1.5 equiv, 0.375 mmol, 65 μL) and 1 mL DMF. The vials were sealed under air with a rubber septum cap and placed in an oil bath preheated to 50° C. Aliquots were removed from each vial at time intervals, diluted with ethyl acetate, and analyzed by gas chromatography with an FID detector. The percent conversion of iodobenzene and t-butyl acrylate to t-Butyl Cinnamate was plotted as a function of time (in minutes) for the Pd/C monoliths prepared as described in Examples 2 and 3. The results are plotted in FIG. 3, and summarized in Table 1 below.

TABLE 1

Catalyst efficiency in coupling of iodobenzene and t-butyl acrylate

| | % t-Butyl Cinnamate by GC | |
|---|---|---|
| Time (min) | Example 2 | Example 3 |
| 120 | 0% | 2% |
| 240 | 4% | 88% |
| 480 | ND | 100% |
| 1440 | 85% | |

ND = not determined

Example 12

Hydrogenation of 4-nitrophenol using Pd/C

A 0.05 g monolith of Pd/C from Example 2 was added to 15 mL water containing 9×10$^{-2}$ millimolar 4-nitrophenol at pH ~8 and placed with stirring under 10 psi of hydrogen gas. After given period of time the monolith was removed and absorbance at 400 nm determined. This experiment was then repeated using the same monolith with fresh solution with the monolith being kept in the stirred solution under hydrogen for 10, 20, 30, 40, 50, 60, 70, 80, 90, 100, 110 and 120 minutes. From these experiments, the turnover number (TON; amount of reactant (moles) divided by the amount of catalyst (moles) times the percent yield of product) and turnover frequency (TOF; TON divided by time (hours)) for the catalyst were calculated.

From these experiments, a turnover number of 0.18 and turnover frequency of 0.18 per hour were determined for the hydrogenation of 4-nitrophenol using the PD/C monolith prepared in Example 2. The same experiments were repeated using a commercial pellet of 1% by weight Pd on activated carbon (obtained from Johnson Matthey). The commercially available pellet of Pd on activated carbon exhibited a turnover number of 0.00037 and turnover frequency of 0.00037 per hour.

0.05 g of the Pd/C monolith prepared in Example 2 was crushed. Similar experiments were performed to evaluate the activity of the crushed monolith. From these experiments, a turnover number of 0.44 and a turnover frequency of 0.44 per hour were determined for the hydrogenation of 4-nitrophenol using the PD/C monolith prepared in Example 2. The same experiments were repeated using a commercially available Pd/C powder catalyst obtained from Sigma-Aldrich Co. (catalog number 20569-9). The commercially available Pd/C powder catalyst was determined to have a turnover number of 0.043 and a turnover frequency of 0.13 per hour.

0.05 g monolith of the Pd/C monolith prepared in Example 3 was suspended in a wire mesh basket, and a similar set of experiments was performed. From these experiments, a turnover number of 0.036 and turnover frequency of 0.036 per hour were determined for the hydrogenation of 4-nitrophenol using the PD/C monolith prepared in Example 3.

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

What is claimed is:

1. A hierarchically porous material comprising:
   a) a plurality of macropores defined by a wall, wherein the macropores have a diameter of from about 0.1 μm to about 50 μm, wherein the macropores interconnect, forming a continuous network of pores that spans the porous material, wherein the walls of the macropores comprise a plurality of mesopores defined by a wall, wherein the mesopores have a diameter of from about 2 nm to about 50 nm, and wherein the walls of the macropores and mesopores comprise a continuous carbon phase; and b) a plurality of discrete nanoparticles dispersed on the carbon phase of the macropores and mesopores, wherein the concentration of the nanoparticles present in an interior region of the hierarchically porous material, measured as the weight percent of metal atoms present in the interior region of the hierarchically porous material as determined using energy dispersive x-ray spectroscopy, is within 50% of the concentration of nanoparticles present on an exterior region of the hierarchically porous material, when measured as the weight percent of metal atoms present on the exterior region of the hierarchically porous material as determined using energy dispersive x-ray spectroscopy.

2. The material of claim 1, wherein the material is a monolith.

3. The material of claim 1, wherein the material is a particle.

4. The material of claim 1, wherein the macropores have a diameter of from about 0.5 μm to about 30 μm.

5. The material of claim 1, wherein the mesopores have a diameter of from about 2 nm to about 15 nm thereby resulting in a porous material with hierarchical pores.

6. The material of claim 1, wherein the nanoparticles comprise a catalytically active metal, metal oxide, or combinations thereof.

7. The material of claim 6, wherein the metal, metal oxide, or combinations thereof comprise a metal selected from the group consisting of Ti, V, Cr, Mn, Fe, Co, Ni, Cu, Zr, Nb, Mo, Tc, Ru, Rh, Pd, Ag, Hf, Ta, W, Re, Os, Ir, Pt, Au, La, Ce, Pr, Nd, Pm, Sm, Eu, Gd, Tb, Dy, Ho, Er, Tm, and Yb.

8. The material of claim 1, wherein the nanoparticles are spherical particles having an average particle size of from about 2 nm to about 50 nm.

9. The material of claim 1, wherein the nanoparticles have a specific surface area of greater than about 1 $m^2/g$ of nanoparticles.

10. The material of claim 1, wherein the nanoparticles have a specific surface area of greater than about 750 $m^2/g$ of nanoparticles.

11. The material of claim 1, wherein the nanoparticles are present in an amount from greater than 0% by weight to about 30% by weight, based on the total weight of the hierarchically porous material.

12. The material of claim 1, wherein the nanoparticles are present in an amount from greater than 0% by weight to about 2.5% by weight, based on the total weight of the hierarchically porous material.

13. A method for producing a hierarchically porous material defined by claim 1, comprising:

(i) contacting a hierarchically porous carbon material with a composition comprising a metal salt at reduced pressure; and (ii) reacting the metal salt to produce metal and/or metal oxide nanoparticles dispersed throughout the hierarchically porous material.

14. The method of claim 13, wherein the metal salt comprises a metal selected from the group consisting of Ti, V, Cr, Mn, Fe, Co, Ni, Cu, Zr, Nb, Mo, Tc, Ru, Rh, Pd, Ag, Hf, Ta, W, Re, Os, Ir, Pt, Au, La, Ce, Pr, Nd, Pm, Sm, Eu, Gd, Tb, Dy, Ho, Er, Tm, Yb, and combinations thereof.

15. The method of claim 13, wherein step (ii) comprises contacting the metal salt with a reducing agent.

16. The method of claim 15, wherein the reducing agent comprises hydrogen gas, alcohol, polyol, carboxylic acid, aldehyde, hydrazine, hydride, ketone, or borane.

17. The method of claim 13, wherein step (ii) comprises heating the hierarchically porous carbon material and metal salt to above the decomposition temperature of the metal salt.

18. A method of performing a Heck coupling reaction comprising contacting an organohalide or pseudohalide and an olefin with a hierarchically porous material defined by claim 1 in the presence of a base and under conditions effective to cross-couple the organohalide or pseudohalide and the olefin, wherein the nanoparticles comprise Pd nanoparticles, Ni nanoparticles, Cu nanoparticles, or combinations thereof.

19. The method of claim 18, wherein the organohalide or pseudohalide comprises an aryl or vinyl halide or pseudohalide.

20. A hierarchically porous material comprising:

a) a plurality of macropores defined by a wall, wherein the macropores have a diameter of from about 0.1 μm to about 50 μm, wherein the macropores interconnect, forming a continuous network of pores that spans the porous material, wherein the walls of the macropores comprise a plurality of mesopores defined by a wall, wherein the mesopores have a diameter of from about 2 nm to about 50 nm, and wherein the walls of the macropores and mesopores comprise a continuous carbon phase; and b) a plurality of discrete nanoparticles dispersed on the carbon phase of the macropores and mesopores, wherein the nanoparticles have a specific surface area of at least about 300 $m^2/g$ of nanoparticles.

* * * * *